(12) United States Patent
Hirthe et al.

(10) Patent No.: US 7,078,910 B2
(45) Date of Patent: Jul. 18, 2006

(54) FLUID FORMULATION EVALUATION AND IMPROVEMENT UTILIZING BROAD SPECTRUM IMPEDANCE SPECTROSCOPY

(75) Inventors: Richard Walter Hirthe, Milwaukee, WI (US); Jianxun Hu, Milwaukee, WI (US); Charles John Koehler, Milwaukee, WI (US); Martin Arthur Seitz, Brookfield, WI (US); David Richard Sosnowski, Lake Orion, MI (US); Ronald Mark Johnson, Rochester Hills, MI (US); David Lee Wooton, Beaverdam, VA (US); Anne Matthews Brunson, Grafton, WI (US)

(73) Assignee: Eaton Corporation, Cleveland, OH (US)

( * ) Notice: Subject to any disclaimer, the term of this patent is extended or adjusted under 35 U.S.C. 154(b) by 90 days.

(21) Appl. No.: 10/793,344

(22) Filed: Mar. 4, 2004

(65) Prior Publication Data

US 2005/0194977 A1 Sep. 8, 2005

(51) Int. Cl.
*G01N 27/02* (2006.01)
*G01R 27/08* (2006.01)

(52) U.S. Cl. ............... 324/446; 324/448; 324/449; 324/698

(58) Field of Classification Search ........ 324/446–449, 324/698
See application file for complete search history.

(56) References Cited

U.S. PATENT DOCUMENTS

| | | | |
|---|---|---|---|
| 4,686,857 A | 8/1987 | Kato | |
| 5,361,628 A | 11/1994 | Marko et al. | |
| 5,660,181 A | 8/1997 | Ho et al. | |
| 5,985,120 A | 11/1999 | Cholli et al. | |
| 6,245,571 B1 | 6/2001 | Roman | |
| 6,278,281 B1 | 8/2001 | Bauer et al. | |
| 6,377,052 B1 | 4/2002 | McGinnis et al. | |
| 6,380,746 B1 | 4/2002 | Polczynski et al. | |
| 6,433,560 B1 | 8/2002 | Hansen et al. | |
| 6,549,861 B1 | 4/2003 | Mark et al. | |
| 6,560,352 B1 | 5/2003 | Rowe et al. | |
| 6,577,112 B1 * | 6/2003 | Lvovich et al. ............ 324/71.1 |
| 6,620,621 B1 | 9/2003 | Cohenford et al. | |
| 6,735,541 B1 | 5/2004 | Kern et al. | |
| 6,820,012 B1 | 11/2004 | Sunshine | |
| 6,844,745 B1 * | 1/2005 | Schachameyer et al. .... 324/698 |
| 6,850,865 B1 | 2/2005 | Hirthe et al. | |
| 2002/0125899 A1 | 9/2002 | Lvovich et al. | |

(Continued)

FOREIGN PATENT DOCUMENTS

EP    1098196 A    5/2001

(Continued)

OTHER PUBLICATIONS

U.S. Appl. No. 10/778,896, filed Feb. 17, 2004, Wooton, et al.

(Continued)

*Primary Examiner*—Anjan Deb
*Assistant Examiner*—Timothy J. Dole
(74) *Attorney, Agent, or Firm*—Jaquez & Associates; Martin J. Jaquez, Esq.; Larry D. Flesner

(57) ABSTRACT

A method and apparatus for evaluating and improving the properties of fluid formulations is disclosed. The inventive concept employs impedance spectroscopy (IS) measurements and data analyses to determine IS parameters of fluids representative of a fluid formulation. Correlations are determined between the IS parameters and the properties of the fluids, and a modified or new fluid formulation may be developed responsive to the correlations.

29 Claims, 32 Drawing Sheets

U.S. PATENT DOCUMENTS

| | | | |
|---|---|---|---|
| 2003/0141882 A1 | 7/2003 | Zou et al. | |
| 2003/0222656 A1* | 12/2003 | Phillps et al. | 324/605 |
| 2004/0239344 A1* | 12/2004 | Hu | 324/698 |
| 2005/0110503 A1 | 5/2005 | Koehler et al. | |

FOREIGN PATENT DOCUMENTS

| | | |
|---|---|---|
| WO | WO 03/014729 | 2/2003 |
| WO | WO 03/104798 | 12/2003 |

OTHER PUBLICATIONS

Jianxun Hu, M.S., "The Characterization of Lubricating Fluids Using AC Impedance Spectroscopy", a dissertation, Dec. 2000, Milwaukee, WI.

"Principal Components Analysis" (downloaded on Nov. 25, 2003) from http://www.okstate.edu/artsci/botany/ordinate/PCA.htm.

Aapo Hyvarinen, "Principal Component Analysis", Apr. 23, 1999 (downloaded on Nov. 4, 2003) from http://www.cis.hut.fi/~aapo/papers/NCS99web/node5.html.

Jaakko Hollmen, "Principal Component Analysis", Mar. 8, 1996 (downloaded on Nov. 4, 2003) from http://www.cis.hut.fi/~jhollmen/dippa/node30.html.

"Principal Component Analysis" (downloaded on Nov. 14, 2003) from http://www.casaxps.cwc.net/FactorAnalysis.htm.

"Principal Components and Factor Analysis" (downloaded Nov. 4, 2003) from http://www.statsoftinc.com/textbook/stfacan.html.

"Algorithms, The Beer Lambert Law" (downloaded on Nov. 26, 2003) from http://www.galactic.com/algorithms/beer_lambert.htm.

"Algorithms, Classical Least Squares (CLS)" (downloaded on Nov. 26, 2003) from http://www.galactic.com/algorithms/cis.htm.

"Algorithms, Discriminant Analysis, The Mahalanobis Distance" (downloaded on Nov. 25, 2003) from http://www.galactic.com/algorithms/discrim_mahaldist.htm.

"Algorithms, Discriminant Alanysis, The PCA/MDR Method" (downloaded on Nov. 25, 2003) from http://www.galactic.com/algorithms//discrim_pca.htm.

"Algorithms, Inverse Least Squares" (downloaded on Nov. 25, 2003) from http://www.galactic.com/algorithms/ils.htm.

"Algorithms, Least Squares Regression" (downloaded on Nov. 25, 2003) from http://www.galactic.com/algorithms/least_squares.htm.

"Algorithms, Partial Least Squares" (downloaded on Nov. 25, 2003) from http://www.galactic.com/algorithms/pls.htm.

"Algorithms, Principal Component Analysis Methods" (downloaded on Nov. 25, 2003) from http://www.galactic.com/algorithms/pca.htm.

"Algorithms, Principal Component Regression" (downloaded on Nov. 26, 2003) from http://www.galactic.com/algorithms/pcr.htm.

Seitz, M.A., et al., "Process-Monitoring Via Impedence Spectroscopy", Materials Research Society Symposium Proceedings, Materials Research Society, Pittsburg, PA; 1996, pp. 57-68.

Wang, et al., "The application of a.c. impedance technique for detecting glycol contamination in engine oil", Elsevier, Sensors and Actuators B 40, May 15, 1997, pp. 193-197.

Australian Coal Research Limited, "Online Monitoring of Lubrication Oil Contamination and Degradation", XP-002329440, retrieved Online at www.acarp.com.au/Completed/abstracts/C9037abstract.htm, Apr. 30, 2002, retrieved on May 23, 2005.

* cited by examiner

FLUID FORMULATION EVALUATION AND IMPROVEMENT UTILIZING BROAD SPECTRUM IMPEDANCE SPECTROSCOPY

CROSS REFERENCE TO RELATED APPLICATIONS

The present application is related to the co-pending U.S. patent application, application Ser. No. 10/723,624, filed Nov. 26, 2003, titled "Fluid Condition Monitoring Using Broad Spectrum Impedance Spectroscopy". application Ser. No. 10/723,624 is commonly owned by the assignee hereof, and is hereby fully incorporated by reference herein, as though set forth in full, for its teachings on statistical techniques for use in performing analysis of Impedance Spectroscopy data. This incorporated application is also provided in full in Appendix A of the present application. This present application is also related to co-pending U.S. patent application, application Ser. No. 10/778,896, filed Feb. 17, 2004, entitled "Fluid Quality Control Using Broad Spectrum Impedance Spectroscopy". application Ser. No. 10/778,896 is commonly owned by the assignee hereof, and is also hereby fully incorporated by reference herein, as though set forth in full, for its teachings on the use of Impedance Spectroscopy data to monitor and control fluid properties and quality.

BACKGROUND

1. Field

The present invention relates to methods and apparatus for monitoring and controlling the properties of fluids, and more particularly to a method and apparatus for evaluating and improving the performance properties of fluid formulations, such as lubricating fluids blended with additives.

2. Description of Related Art

When developing fluid formulations, such as lubricating fluids blended with additives, analytical testing is required to ascertain that the properties of the blended lubricant are consistent with intended design properties. Lubricant formulations typically include selected additives based on the requirements of the intended application for the lubricant. All of the additives included have particular performance properties that are exploited in the final fluid formulation design. To improve the performance properties of fluid formulations, it is necessary to observe, measure and understand the combined functional effects of the additives on the physical properties of the formulation. Modifying the additives and/or the blended fluid formulation, based on observation and understanding of the additive effects, can improve both the performance and cost effectiveness of the lubricant product.

Systems for in-situ (e.g., performed in an operating system, such as an engine or transmission) monitoring the properties of lubricating fluids are known. One such system is disclosed in U.S. Pat. No. 6,278,281 entitled "Fluid Control Monitor" issued to Bauer, et al. Bauer describes a technique employing AC electro-impedance spectroscopy (referred to hereinafter as impedance spectroscopy or "IS"), and is implemented using probe electrodes that are placed in contact with a fluid under test. The method of operation includes making IS measurements at a first frequency that is less than 1 Hz and at a second frequency that is greater than 1 Hz, comparing the two IS measurements, and declaring a "pass" or "fail" condition based on a previously determined empirical relationship. This prior art lubricating fluid monitoring system disadvantageously effectively analyzes only a single property of the IS spectra based on the difference of two IS measurements. Consequently, the IS measurement technique taught by Bauer is not capable of determining the complex properties of compound fluids, as is required when designing fluid formulations having a plurality of additives.

A co-pending and commonly assigned U.S. Patent Application, application Ser. No. 10/723,624, filed Nov. 26, 2003, entitled "FLUID CONDITION MONITORING USING BROAD SPECTRUM IMPEDANCE SPECTROSCOPY," teaches a broad spectrum IS method for determining IS parameters relating to the bulk and interfacial properties of fluids. When developing a performance-based combination of one or more additives in a base fluid, referred to herein as a "formulation," interactions between a single additive and the base fluid, or between a plurality of additives themselves, can cause unexpected results in the performance properties of the formulation. Because the performance of the formulation depends on both the properties of both its bulk and interface, a method is needed to accurately evaluate these properties with regard to the effects of the additives, singly and in plurality. Therefore, a need exists for a method and apparatus evaluating and improving fluid formulations and additives.

SUMMARY

A method and apparatus evaluating and improving the properties of fluid formulations is disclosed. The inventive concept employs impedance spectroscopy (IS) measurements and data analyses to determine IS parameters for fluids representative of a fluid formulation. Correlations are determined between the IS parameters and the properties of the fluids, and a new fluid formulation may be developed based on these correlations.

In one exemplary embodiment, IS measurements at three or more frequencies are made using probe electrodes in contact with fluids representative of a fluid formulation. The IS data are analyzed using statistical techniques, equivalent circuit modeling techniques, or a combination thereof. The data analysis provides at least one IS parameter indicative of at least one fluid property for the fluids. At least one correlation is determined between one or more IS parameters and one or more properties of the fluids. A new fluid formulation is developed, responsive to correlations between the IS parameters and the properties of the fluids.

DETAILED DESCRIPTION

Throughout this description, embodiments and variations are described for the purpose of illustrating uses and implementations of the inventive concept. The illustrative description should be understood as presenting examples of the inventive concept, rather than as limiting the scope of the concept as disclosed herein.

Figure 1:
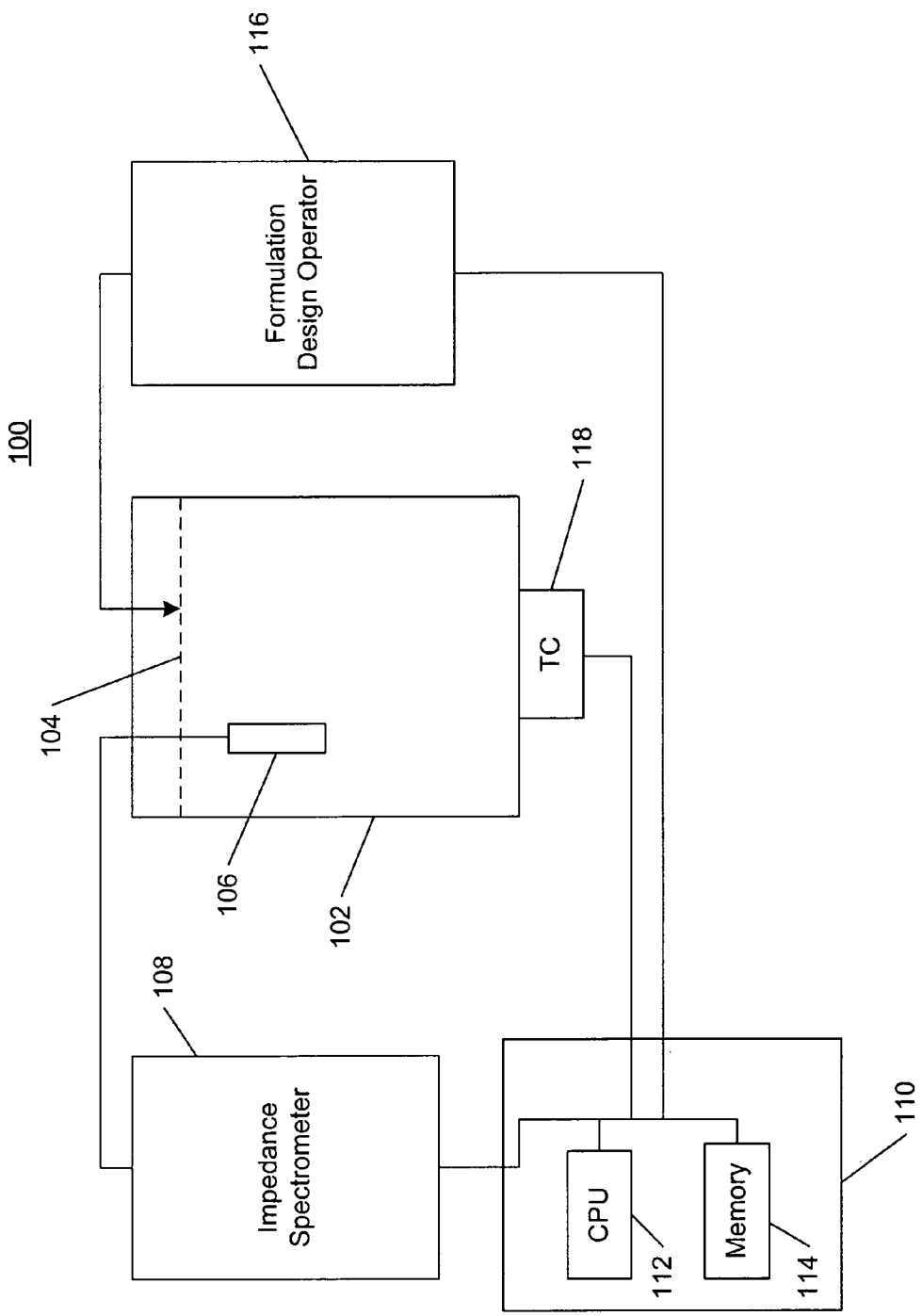
FIG. 1 is a block diagram of a simplified system evaluating and improving fluids based on impedance spectroscopy.

FIG. 1 shows a block diagram of a simplified formulation evaluation and improvement system 100 based on fluid properties determined using IS measurements and analysis. A fluid container 102 may comprise a glass or metal container, blending tank, or an in-line container, such as a pipe. The container 102 contains a fluid 104 representative of a fluid formulation, such as a lubricant with additives. The fluid 104 may be a fluid selected from a plurality of fluids representative of one or more fluid formulations. For use in performing IS measurements and experimental operations, the fluid 104 is typically maintained at a constant temperature using a temperature sensor and controller 118. The temperature sensor and controller 118 is in contact with the container 102 or the fluid 104. The temperature setting for the controller 118 may be set by a system operator (not shown), or it may be set using a data processing system 110 operatively coupled to the controller 118. A measured temperature from the device 118 may be conveyed to the processing system 110.

An IS probe 106 is in contact with the fluid 104. Many suitable IS probes are known to those skilled in the electrochemical arts. U.S. Pat. No. 6,278,281 entitled "Fluid Control Monitor" issued to Bauer, et al., on Aug. 21, 2001, describes a plurality of suitable electrode probes that may be used in conjunction with the present invention. An exemplary IS probe device design utilizing concentric tubular electrodes is disclosed in U.S. patent application Ser. No. 2003/0141882, 10/060107, filed Jan. 31, 2002, entitled "Probe Assembly for a Fluid Condition Monitor and Method of Making Same." Both the issued patent and the published patent application cited above are commonly owned by the assignee hereof, and both are hereby fully incorporated by reference herein as though set forth in full, for their teachings on IS probe devices, and for their teachings on methods and equipment relating to IS measurements of fluids. Other exemplary IS probe designs include parallel plate electrodes, interdigitated electrodes and spiral electrodes.

As shown in FIG. 1, the IS probe 106 is operatively coupled to an impedance spectrometer 108. The construction and operation of impedance spectrometers are well known to persons skilled in the electrochemical arts, and commercial impedance spectrometers are available. IS instrumentation generally comprises an array of impedance and frequency response analyzers, as well as "lock-in" amplifiers. The equipment provides a source of AC signals of varying frequency. The IS equipment also provides circuitry for detecting the magnitude of electric current conducted through the sample. An exemplary combination of IS instrumentation may include an EG&G Potentiostat/Galvanostat Model 283 (EG&G is a Division of URS Corporation, of San Francisco, Calif.), and a Solartron Impedance/Gain-Phase Analyzer Model 1260 (hereinafter, Solartron 1260—Solartron Analytical is a member of the Roxboro Group plc, of Cambridge, United Kingdom). The Solartron 1260 provides an AC signal of varying frequency. Signal levels ranging from 125 mV (in fully formulated lubricating fluids) to 1000 mV (in the base fluid) have been found to produce well-defined IS data. The impedance spectrometer 108 is operatively coupled to a data processing system 110. In one embodiment, the data processing system 110 comprises a personal computer (PC). IS data acquisition may be accomplished using commercial PC-based computer programs such as "Z-Plot™", and "Z-View™" (see, for example, the operating manual entitled "Zplot for Windows," *Scribner Associates, Inc.*, version 2.1, 1998), as well as other software that may be custom-developed by persons skilled in the arts of scientific data acquisition. These PC-based computer programs for IS data acquisition are well known in the art.

As shown in FIG. 1, in one embodiment, the data processing system 110 includes a central processing unit (CPU) 112 and a memory 114, both of which are operatively coupled to receive data from the impedance spectrometer 108, and configured to output data to a formulation design operator 116. The memory 114 stores software instructions used for acquiring data. The memory 114 also may be used to store data from measurements performed sequentially on a plurality of fluids 104, software for data analysis functions, and data analysis results for a plurality of fluids 104. These functions are described more fully hereinbelow.

The formulation design operator 116 may comprise one or more persons, an apparatus, or any combination thereof. The results of IS data analyses performed by the data processor 110 are output to the operator 116, and the operator 116 may develop or produce a modified, improved, or new fluid formulation 120, in accordance with teachings hereinbelow.

Exemplary Data

Figure 2:
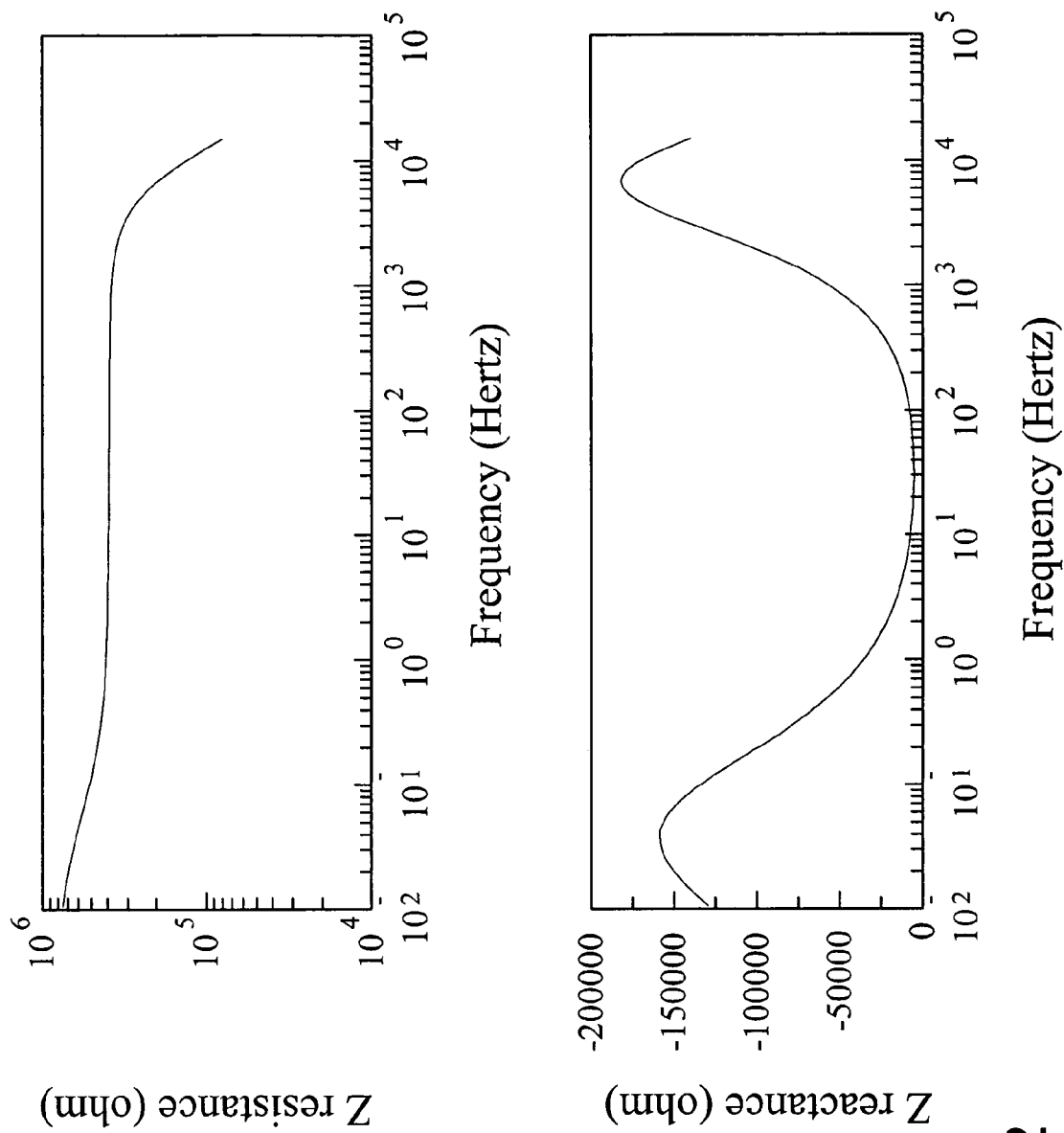
FIG. 2 is an illustration of typical impedance spectroscopy data shown as a Bode plot.

Referring now to FIG. 2, typical IS data are illustrated in the form of Bode plots, which are well-known to persons skilled in the electronic arts. The upper plot shows the resistive part of impedance versus the logarithm of frequency. The lower plot shows the reactive part of impedance versus the logarithm of frequency. These exemplary data represent an IS spectrum for a given lubricant fluid.

Although the data are shown in FIG. 2 as continuous curves, persons skilled in the arts of scientific data acquisition will understand that the curves actually represent a plurality of connected point measurements. For example, the curves may comprise ten data points per decade. Alternatively, far fewer points may be employed, as for example are used in U.S. Pat. No. 6,278,281 cited above, wherein only two points are used. In some exemplary embodiments of the present invention, IS spectra data includes at least three points, and typically tens or hundreds of points are used. More than a few hundred points typically are not required. For the practice of the present invention, the IS spectra points will generally (although exceptions may occur) span a frequency range sufficient to represent IS parameters associated with both the bulk fluid and the interface between the fluid and the electrode (the fluid/electrode interface). These IS parameters, and their frequency ranges, are described in more detail below. In general, the IS spectra includes frequencies that are both above and below 1 Hz.

Figure 3:
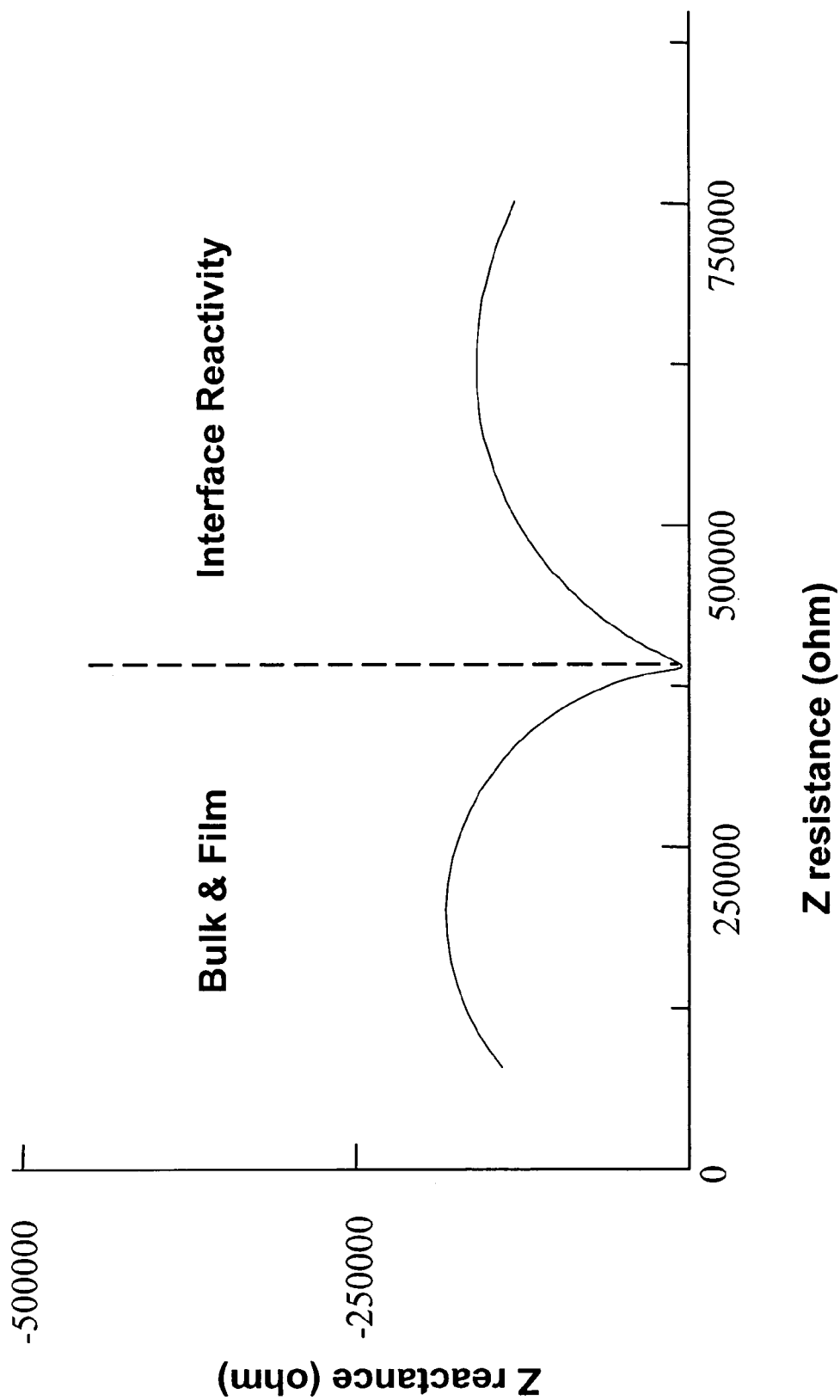
FIG. 3 is an illustration of typical impedance spectroscopy data shown as a Nyquist plot.

FIG. 3 illustrates the same IS data depicted in FIG. 2 using a Nyquist plot, which is well known to persons skilled in the electronic arts. The data show a minimum in the reactance, known as the "Nyquist minimum". As described below in more detail, data for frequencies lower than the Nyquist minimum can be associated with an interface reactivity caused by electrically-active phenomena occurring at the fluid/electrode interface. Data for frequencies greater than the minimum can be associated with the electrical properties of the fluid bulk, and with a fluid film present on the electrode.

Exemplary Data Analysis Using Equivalent Circuit Modeling

Figure 4:
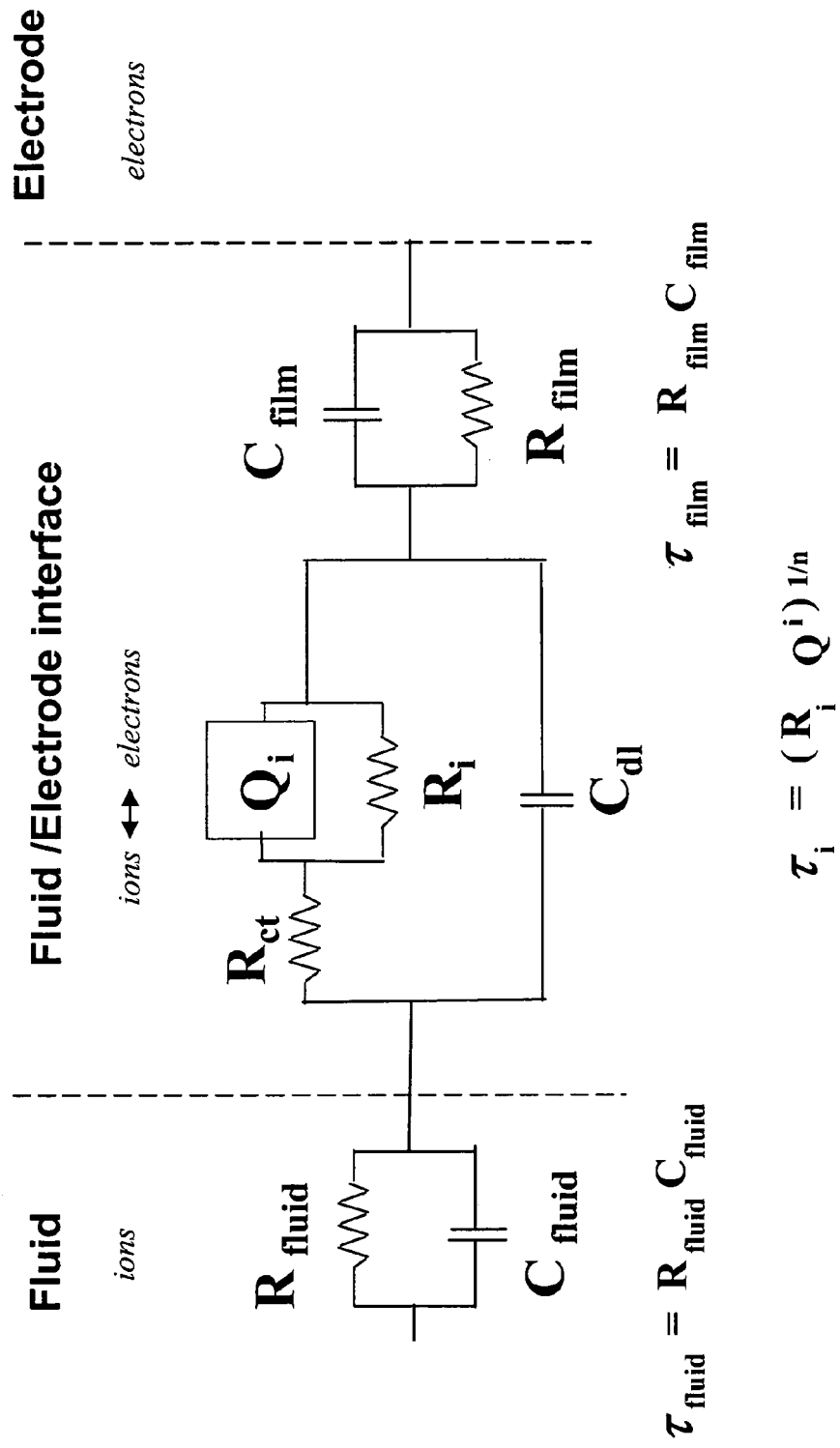
FIG. 4 is an illustration of an equivalent circuit for modeling impedance spectra data.

FIG. 4 shows an equivalent circuit model that may be used to assist data analysis in accordance with one embodiment of the present invention.

As shown in FIG. 4, there is an impedance, associated with the bulk fluid electrical properties, comprising $R_{fluid}$ and $C_{fluid}$, having a time constant $\tau_{fluid}$ as follows:

$$\tau_{fluid} = R_{fluid} C_{fluid}$$

Persons skilled in the electrochemical arts shall recognize that for many fluids, such as lubricating fluids, the bulk electrical transport occurs primarily via ionic conduction. For fluids exhibiting ionic conduction there is also impedance associated with the fluid/electrode interface. The electrical phenomena resulting from contact between the fluid and the electrode surface is represented in FIG. 4 by elements shown between the vertical dashed lines. The interfacial impedance includes a capacitance $C_{dl}$ created by polarization arising from a double layer formation, as ions orient themselves in response to the presence of the charged metal surface. Because the fluid is an ionic conductor and the electrode an electronic conductor, a charge transfer reaction must be operative for current to flow across the fluid/electrode interface. This current leakage across the fluid/electrode interface is represented in FIG. 4 by a parallel path.

As shown in FIG. 4, charge transport is accompanied by energy that is required for charge transfer, represented by a resistance $R_{ct}$, and possibly adsorption, and possibly diffusion as detectable steps in the overall process. The specific nature of this electro chemical reaction determines the form of the detected impedance associated with this reaction path. If the reaction is fast, a diffusion-limited character is often evident. Conversely, reactions involving slow kinetics, i.e., reactions involving rate-limiting adsorption of intermediate species, yield impedance character of a different form. When sufficiently defined from measured data, an interface time constant value $\tau_i$ can be defined in a manner that is analogous to the bulk value. The interface time constant $\tau_i$ reflects either the heterogeneous rate constant of the reaction at the interface, or the magnitude of the diffusion coefficient for the reacting species (reactant or product). This provides an effective value for the net reactivity of species at the fluid/electrode interface, and is calculated from the following relationship:

$$\tau_i = (R_i Q_i)^{1/n},$$

where observed values of n range between 0.5–1.0. The observation of diffusion as rate limiting implies that the rate of reaction at the surface is fast as the potential is modulated by an AC signal, such that local depletion (or accumulation) of the surface-active species occurs. The presence of this diffusion gradient in concentration is observed in the measured impedance as a Constant Phase Element (CPE), denoted as $Q_i$, where the CPE exponent n is equal to 0.5. The determination of n-values for interfacial phenomena at or close to unity is indicative of adsorption, rather than diffusion, as the rate-limiting step at the electrode. To summarize, n-values approximating 0.5 indicate that diffusion is the rate limiting process, n-values approximating 1.0 indicate that adsorption and surface reaction is the rate limiting process, while values for n between 0.5 and 1.0 indicate that both processes are significant as regards the rate limiting process.

Referring again to FIG. 4, another interface time constant, $\tau_{film}$, may also be observed. For appropriately configured measurements and fluid samples, this value is determined according to the following equation:

$$\tau_{film} = R_{film} C_{film},$$

where the resistance $R_{film}$, and the capacitance $C_{film}$, reflect the electrical properties and geometry of the fluid film that may form on the electrode.

Impedance data analysis in accordance with the above described equivalent circuit model may be performed by the data processing system 110 of FIG. 1, using, as an example, the well known Complex Non-Linear Least Squares fitting technique employed by the PC-based computer program, "Equivalent Circuit", written by Boukamp (B. A. Boukamp, "Equivalent Circuit (Equivckt.PAS)" User's Manual, Dept. of Chemical Technology, Universiteit Twente, Netherlands, 1988 and 1989. This fitting technique is also described in an article written by B. A. Boukamp, "A Nonlinear Least Squares Fit procedure For Analysis of Immitance Data of Electrochemical Systems" Solid State Ionics, Vol. 20, pp. 31–44, 1986). The above-cited User's Manual and article are incorporated by reference herein for their teachings on data analysis.

The results of the equivalent circuit data analysis technique described above include values for the circuit elements shown in FIG. 4. These values are referred to herein generally as "IS parameters," and more specifically as "equivalent circuit IS parameters." These equivalent circuit IS parameters may include, without limitation, the following: a bulk fluid resistance $R_{fluid}$, a bulk fluid capacitance $C_{fluid}$, a bulk fluid time constant $\tau_{fluid}$, an interface capacitance $C_{dl}$, a charge transfer resistance $R_{ct}$, an interface time constant $\tau_i$, an interface resistance $R_i$, a Constant Phase Element $Q_i$, a Constant Phase Element exponent n, a film time constant $\tau_{film}$, a film resistance $R_{film}$, and a film capacitance $C_{film}$. Equivalent circuit IS parameters, and other IS parameters described below, may be related to fluid properties, in accordance with teachings presented in more detail below. The equivalent circuit model and corresponding data analysis given above is by way of example only. The scope of the present invention also encompasses the use of other equivalent circuit models and associated analysis methods, software, and techniques that suitably represent IS measurements and properties of fluids.

Exemplary Data Analysis Using Statistical Techniques

In addition to the equivalent circuit data analysis technique described above, the data analysis processes implemented by the data processing system 110 may include one or more well known statistical techniques. For example, the data analysis performed by the data processing system 10 may include, without limitation, the following techniques: Principal Component Analysis (PCA), Multivariate Least Squares Regression (MLR), Principal Component Regression (PCR), Group Method for Data Handling (GMDH), Pattern Recognition analysis, Cluster analysis, and Neural Net analysis. A description of these techniques in reference to IS data analysis is disclosed in the incorporated and co-pending U.S. Patent Application, application Ser. No. 10/723,624, filed Nov. 26, 2003, titled "FLUID CONDITION MONITORING USING BROAD SPECTRUM IMPEDANCE SPECTROSCOPY". This above-incorporated application is set forth in full in Appendix A of the present application.

Exemplary commercially available software that may be used by the data processing system 110 of FIG. 1 in implementing the processes required for the statistical analysis techniques include the following software applications: "The Unscrambler™" by Camo Process™, AS; Norway; Spectrum Quant+™ by PerkinElmer™, Inc., Norwalk, Conn.; and MatLab™ by Mathworks™, Inc., Natick, Mass.

Data analysis using statistical techniques also provides IS parameters that may be related to fluid properties. Examples of such IS parameters obtained from statistical techniques are described in reference to exemplary data presented hereinbelow.

Exemplary Implementations

This section presents data and analyses that exemplify embodiments of the present inventive concept in conjunction with lubricating oil formulations. IS measurements are performed on the fluids, the IS data obtained are analyzed to determine IS parameters that are indicative of fluid properties, and the fluid properties are correlated to formulation components and properties. The inventive process provides information that may be used to modify formulations and develop new formulations.

EXAMPLE 1

Base Fluid Plus Antioxidant

Figure 5:
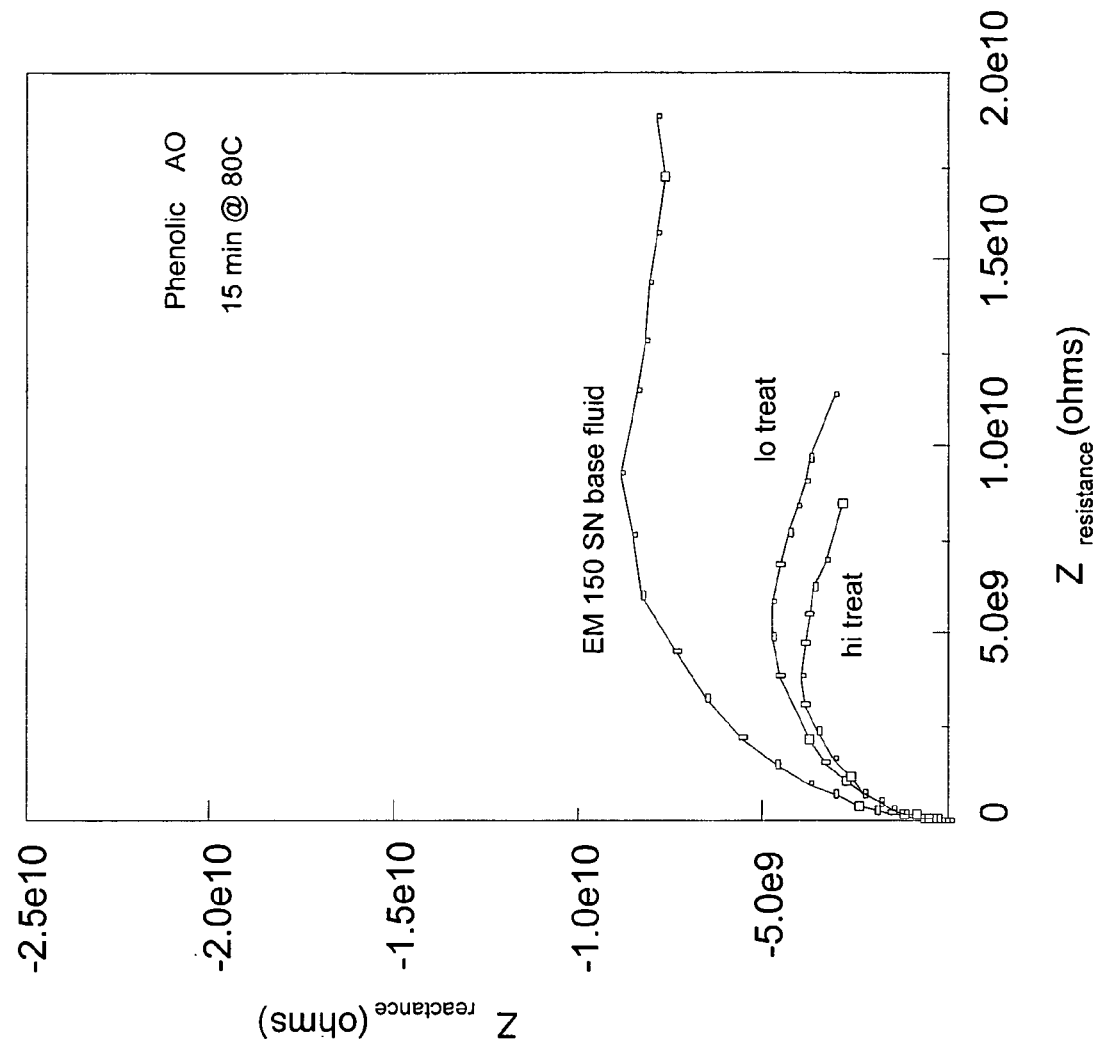
FIG. 5 is a plot of typical impedance spectroscopy data obtained for a base oil and for two concentrations of an anti-oxidant in the base oil.

FIG. 5 illustrates IS data obtained for a base fluid and formulation comprising two concentration levels of a Phenolic antioxidant (AO) added to the base fluid. LoTreat of the phenolic antioxidant is 0.5% and HI treat is 1.0%. The base fluid, EM 150 SN, is a mildly hydrofinished 150 solvent neutral, hydrocarbon base stock. The data exhibits a semi-circular trace at high frequencies, indicative of the electrical properties of the fluid bulk, and a low frequency tail, indicative of an additional interfacial contribution to the measured impedance. As persons skilled in the art will understand, this is the expected lumped response when the time constant values for the bulk and interface are within two orders of magnitude.

Figure 6:
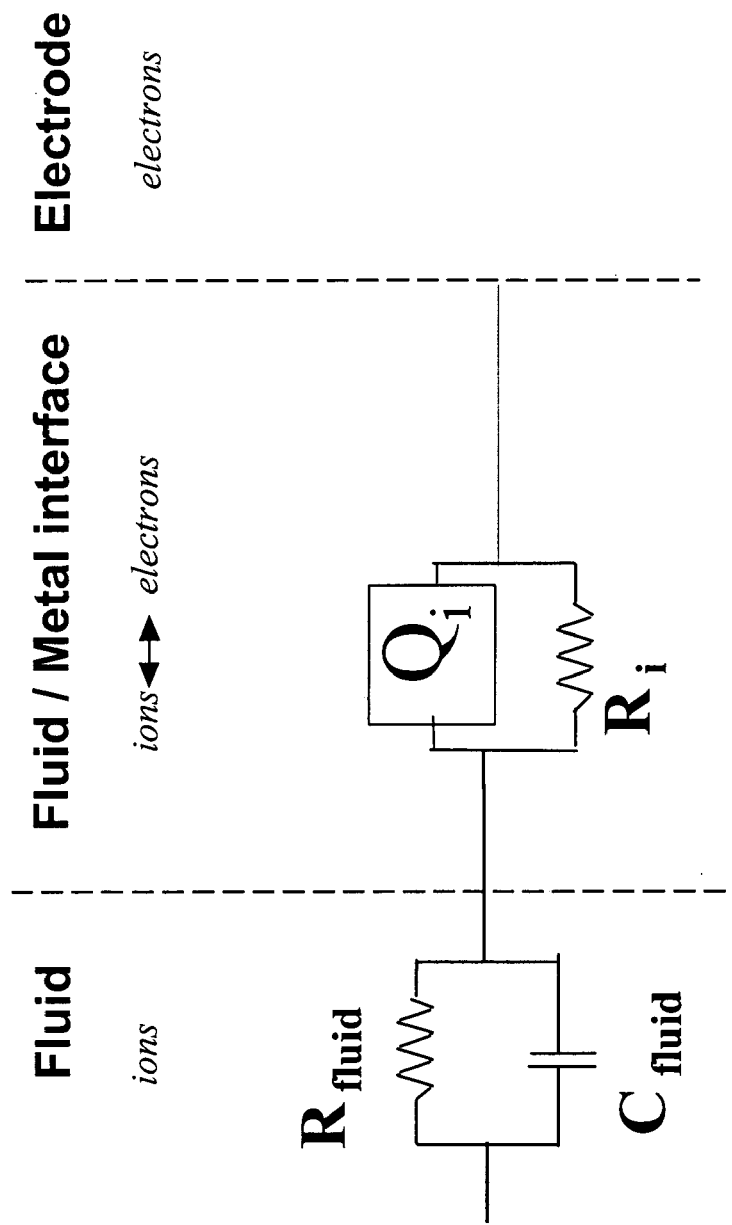
FIG. 6 is an illustration of a first alternative equivalent circuit for modeling impedance spectra data.

The data of FIG. 5 may be analyzed according to a simplified equivalent circuit model as illustrated in FIG. 6, and the IS parameters obtained thereby are shown in TABLE 1.

TABLE 1

IS Parameters for Base Fluid and Base Fluid Plus AO

| FLUID | $R_{fluid}$ (ohms) | $C_{fluid}$ (farads) | $\tau_{fluid}$ (sec) | $R_i$ (ohms) | $Q_i$ (farads) | $\tau_i$ (sec) | n |
|---|---|---|---|---|---|---|---|
| Base Fluid | $1.34 \times 10^{10}$ | $1.4 \times 10^{-10}$ | 1.88 | $7.83 \times 10^9$ | $9.46 \times 10^{-10}$ | 7.41 | 1.0 |
| Base Fluid plus AO, low conc. | $7.5 \times 10^9$ | $1.39 \times 10^{-10}$ | 1.05 | $3.85 \times 10^9$ | $9.86 \times 10^{-10}$ | 3.79 | 1.0 |
| Base Fluid plus AO, high conc. | $6.25 \times 10^9$ | $1.42 \times 10^{-10}$ | 0.87 | $2.76 \times 10^9$ | $9.23 \times 10^{-10}$ | 2.54 | 1.0 |

As shown in TABLE 1, adding AO to the base fluid reduces the resistance of the bulk fluid without significantly modifying the capacitance. In the Table, the ion concentration increase is seen from the resistance decrease, since the mobility relates to viscosity, and there was no observable viscosity difference between the formulations. Likewise, the interfacial impedance is reduced by the AO additive. The CPE exponent n (described above) is found to be unity for all three fluids. As noted above, the determination of n-values for interfacial phenomena at or close to unity is indicative of adsorption (interface reaction rate) as the rate-limiting step at the electrode. Thus, the change in interface impedance caused by the AO additive reflects a change in the net rate of reaction (approximately a factor of two increase), as is determined by comparing the calculated interface time constant values to that of the base fluid.

In this example, the relative interface reaction rate exemplifies a fluid property, responsive to formulation properties such as AO additive concentration, that may be obtained from the IS parameters shown in TABLE 1. Further, the relative bulk resistivities of the fluids are indicated by the IS parameters $R_{fluid}$ shown in the table. Bulk resistivities are modified by ion concentrations and ion mobilities. Thus, ion concentrations and ion mobilities are also exemplary fluid properties, dependent on formulation additives, that can be determined from the IS parameters.

EXAMPLE 2

Base Fluid Plus Detergents

Figure 7:
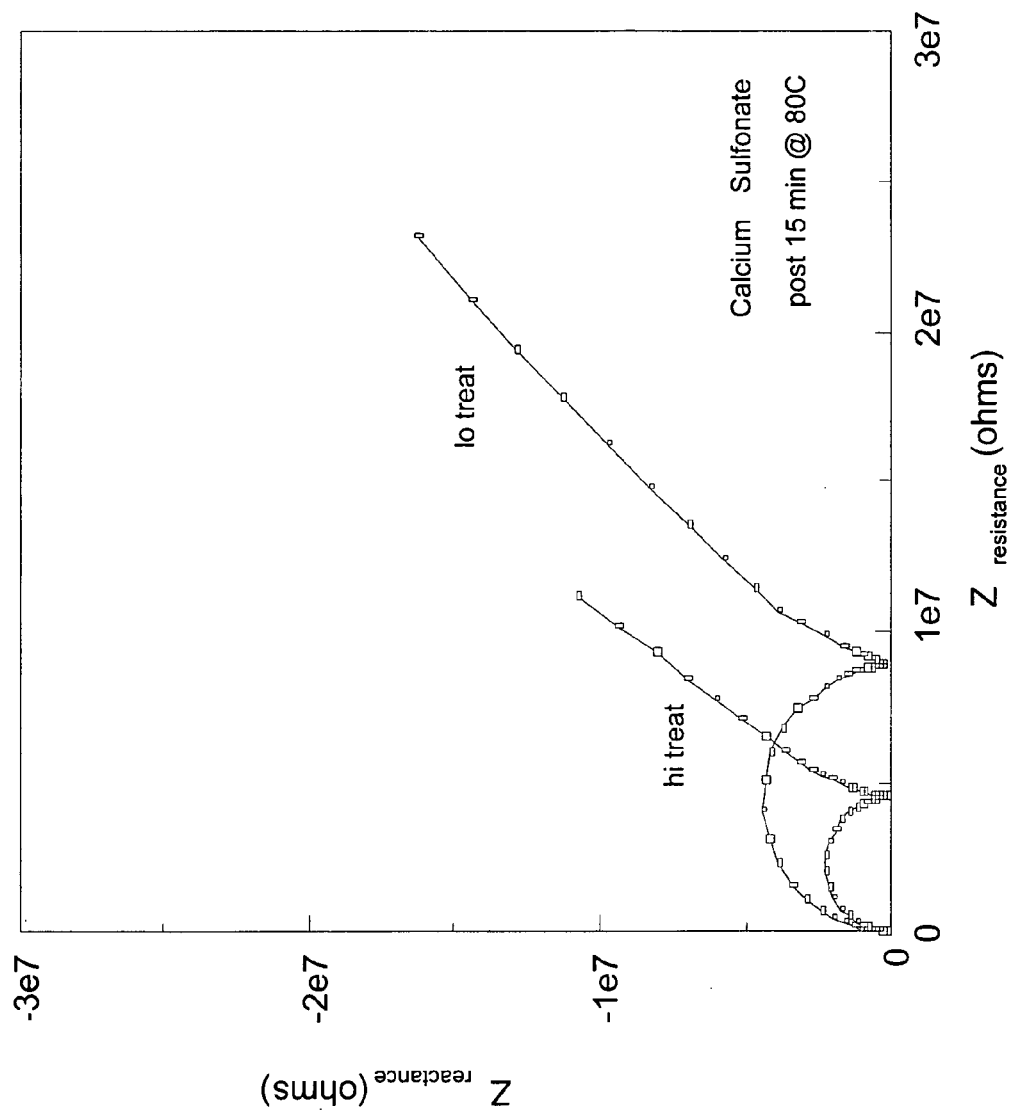
FIG. 7 is a plot of typical impedance spectroscopy data obtained for two concentrations of a calcium sulfonate detergent in a base oil.
Figure 8:
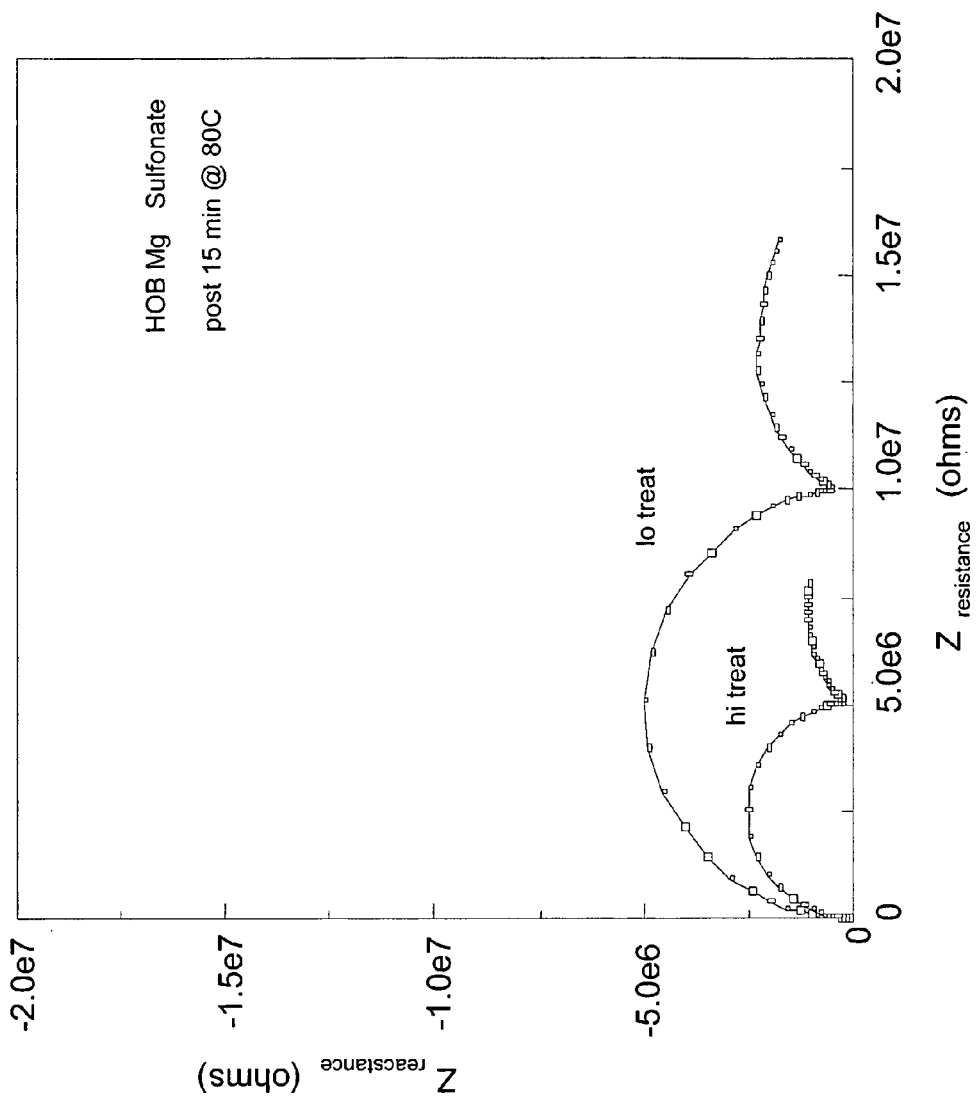
FIG. 8 is a plot of typical impedance spectroscopy data obtained for two concentrations of a magnesium sulfonate detergent in a base oil.

FIGS. 7 and 8 show IS data illustrating the effects of two different detergent additives, each at two different concentration levels, using the same base fluid as used in Example 1 described above. The base fluid data are not shown in these Figures because it would be off scale. Because the base fluid is the same as used in Example 1 above, the data illustrated in FIG. 5 is representative thereof. For FIG. 7 the detergent additive is calcium sulfonate, and for FIG. 8 the detergent additive is HOB magnesium sulfonate. Lo treat of the detergent is 3% and hi treat is 6%. The detergent in FIG. 7 was a commercially available neutral, synthetic calcium alkylbenzene sulfonate. The detergent in FIG. 8 was a commercially available highly overbased, synthetic magnesium alkylbenzene sulfonate. The terminology HOB indicates a highly overbased detergent type. The IS parameters obtained from the data of FIGS. 7 and 8 are shown in TABLE 2 below. For these data analyses, the simplified equivalent circuit model illustrated in FIG. 6 is used.

TABLE 2

Exemplary IS Parameters for Base Fluid and Base Fluid Plus Detergents

| FLUID | $R_{fluid}$ (ohms) | $C_{fluid}$ (farads) | $\tau_{fluid}$ (sec) | $R_i$ (ohms) | $Q_i$ (farads) | $\tau_i$ (sec) | n |
|---|---|---|---|---|---|---|---|
| Base Fluid | $1.34 \times 10^{10}$ | $1.4 \times 10^{-10}$ | 1.88 | $7.83 \times 10^9$ | $9.46 \times 10^{-10}$ | 7.41 | 1.0 |
| Base Fluid plus Ca sulfonate, low conc. | $8.39 \times 10^6$ | $1.28 \times 10^{-10}$ | $1.11 \times 10^{-3}$ | $3.47 \times 10^7$ | $3.85 \times 10^{-7}$ | 19.6 | 0.87 |
| Base Fluid plus Ca sulfonate, high conc. | $4.44 \times 10^6$ | $1.26 \times 10^{-10}$ | $5.51 \times 10^{-4}$ | $4.73 \times 10^7$ | $5.90 \times 10^{-7}$ | 69.9 | 0.78 |
| Base Fluid plus HOB Mg sulfonate, low conc. | $9.96 \times 10^6$ | $1.27 \times 10^{-10}$ | $1.23 \times 10^{-3}$ | $8.34 \times 10^6$ | $2.03 \times 10^{-7}$ | 2.88 | 0.5 |
| Base Fluid plus HOB Mg sulfonate, high conc. | $5.03 \times 10^6$ | $1.30 \times 10^{-10}$ | $6.33 \times 10^{-4}$ | $4.78 \times 10^6$ | $5.18 \times 10^{-7}$ | 6.13 | 0.5 |

The exemplary IS parameters shown in Table 2 indicate that the detergent additives reduce the bulk resistivity of a formulation, relative to the bulk resistivity of the base fluid, by approximately three orders of magnitude, with only a small effect upon the bulk capacitance. The changes in bulk resistivity can be interpreted as an increase in ion concentration. This ion concentration implies the amount of free neutral salts in the bulk formulation. The 6% concentration of HOB magnesium sulfonate has a neutral salt concentration between the 3% neutral sulfonate and the 6% neutral sulfonate. On the other hand, the interface resistivity implies the amount of salts on the interface. The concentration of interface ions relates to the amount of detergent's carbonate in the formulation. Other data (not shown in Table 2) indicates that engine oil that has been formulated with a complete set of additives typically exhibits interfacial behavior that is limited by the rate of transport (diffusion) to/from the metal electrode surface (i.e., as noted above, the CPE exponent n has a value of approximately 0.5). The exemplary IS parameters of TABLE 2 indicate that detergent addition alone causes interfacial behavior indicative of adsorption as the rate limiting factor (and/or a mixture of adsorption and diffusion, i.e. corresponding to CPE exponent n-values in a range approximating 0.75), resulting in longer interfacial time constant values, typically on the order of 10 to 100 seconds. While this fluid property was found for the majority of the detergents investigated, the HOB Mg sulfonate causes interfacial behavior indicative of higher reactivity, where diffusion is rate-limiting, as indicated by CPE exponent n-values of 0.5 in TABLE 2 for the HOB Mg sulfonate formulations. This result suggests that other, undetermined, surface-active species may be present in these formulations, perhaps incorporated via the process oil used to carry the HOB Mg sulfonate additive. This result thus illustrates that the fluid properties determined using the present inventive method provide useful information for screening additive composition and performance.

In this example, as in the previous example, the relative interface reaction rate exemplifies a fluid property, responsive to the formulation design and additives, that may be obtained using the exemplary IS parameters shown in TABLE 2. Likewise, the relative bulk resistivities for the fluids can be determined from the IS resistance values $R_{fluid}$ shown in Table 2. Thus, the bulk resistivity (indicative of ion concentrations and mobilities) is also an exemplary fluid property that can be determined from the IS parameters according to this example. The product of ion concentrations and ion mobilities is another fluid property that can be determined. Ion mobility is related to viscosity of the fluid, which can be observed by other means well known to persons skilled in the arts of petroleum engineering. If it is known that the viscosity and ion mobilities are relatively constant, than the inventive method can be used to determine changes in ion concentrations based on observed changes in $R_{fluid}$ and bulk resistivity.

EXAMPLE 3

Thermal Decomposition of ZDDP in a Base Fluid

Zinc dithiodialkylphosphates (ZDDPs) comprise multifunctional additives used in lubricating fluids. They act as antioxidants, improving the wear inhibition of the lubricant, and protecting metals against corrosion. In this example, a formulation including a high-level concentration of secondary ZDDP additive is heated to 120 degrees Celsius for various periods to observe changes in fluid properties caused by a thermal decomposition test. Lo treat of the ZDDP is 0.62% and hi treat is 1.24%. The term "secondary" is a compound/product definition of the ZDDP that describes its chemical make-up of the alkyl group attached to the phosphorous. An alkyl group can be primary, secondary, tertiary or aryl. The present example teaches the use of IS parameters in determining changes in fluid properties as a function of time during thermal decomposition.

Figure 9:
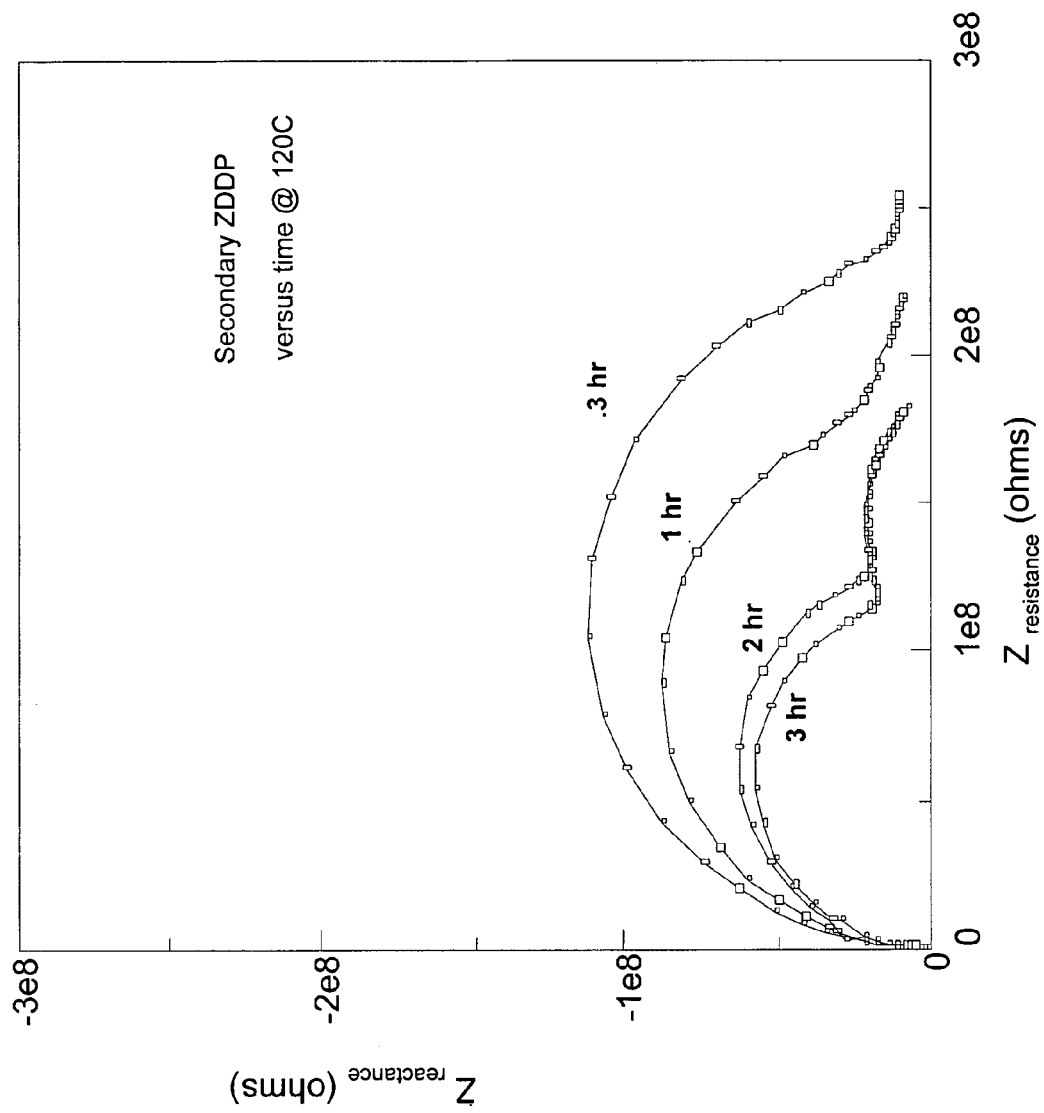
FIG. 9 is a first time series of impedance spectroscopy data for thermal decomposition in a formulation containing ZDDP.
Figure 10:
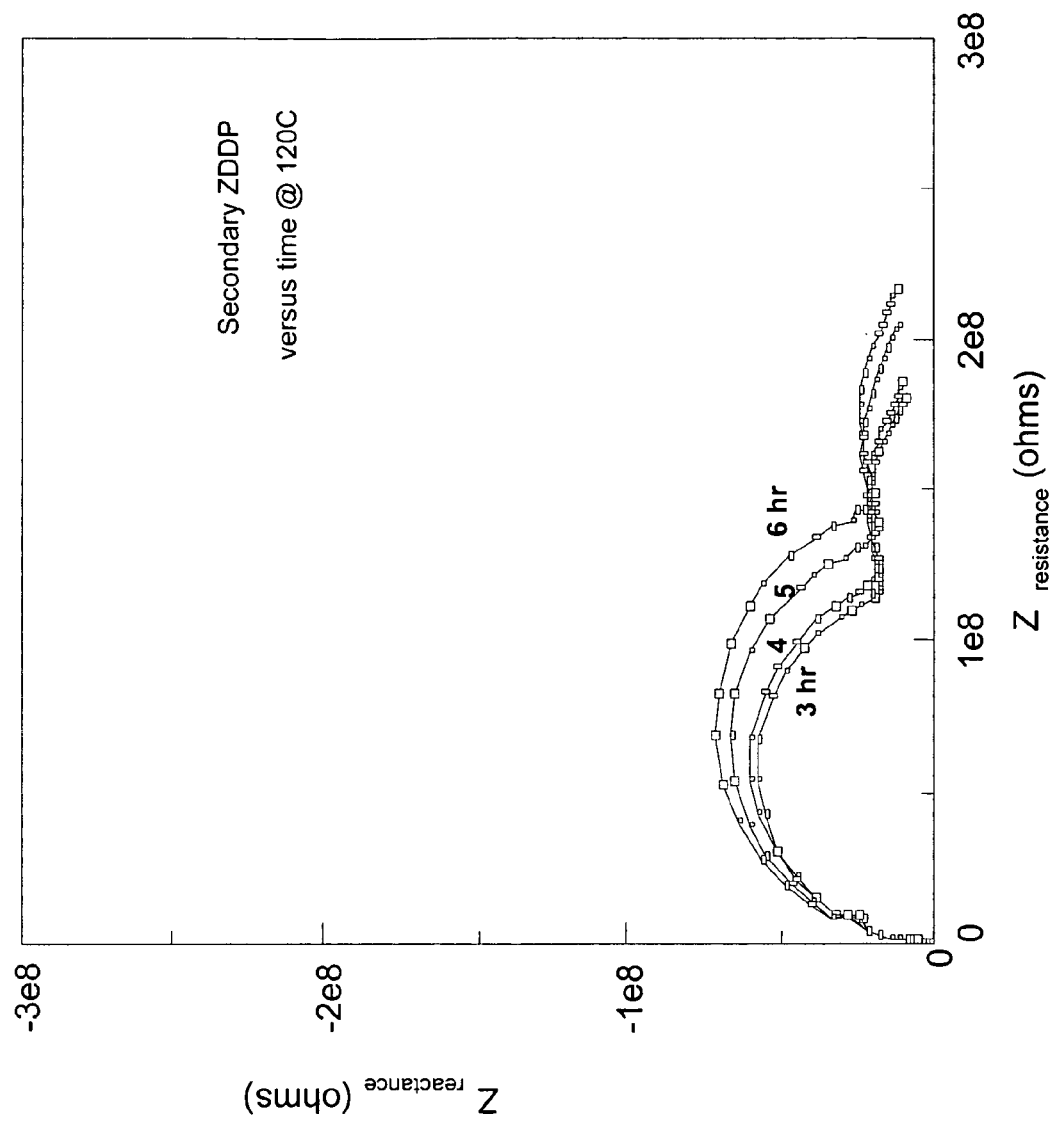
FIG. 10 is a second time series of impedance spectroscopy data for thermal decomposition of a formulation including ZDDP.

In this example, the base fluid containing the high treat (concentration) level of secondary ZDDP is heated to a temperature of 120 degrees Celsius. Following IS probe immersion, IS impedance measurements are conducted for a period of six hours at temperature. Exemplary IS data measured at 0.3, 1.0, 2.0 and 3.0 hours at temperature are shown in FIG. 9. Exemplary IS data measured at 3.0, 4.0, 5.0 and 6.0 hours at temperature are shown in FIG. 10. These data indicate that the bulk impedance of the fluid decreases for approximately 3 hours (FIG. 9), and then increases for the balance of the testing period (FIG. 10). In the absence of viscosity changes, this behavior suggests the initial generation of ions in the fluid, followed by depletion of ions, as exposure of the fluid to the metal electrode of the IS probe ensues at temperature. Simultaneously, as described further below, the character of the interfacial contribution to the measured impedance is found to emerge as the bulk resistance drops, changing only slightly after two hours at temperature.

Figure 11:
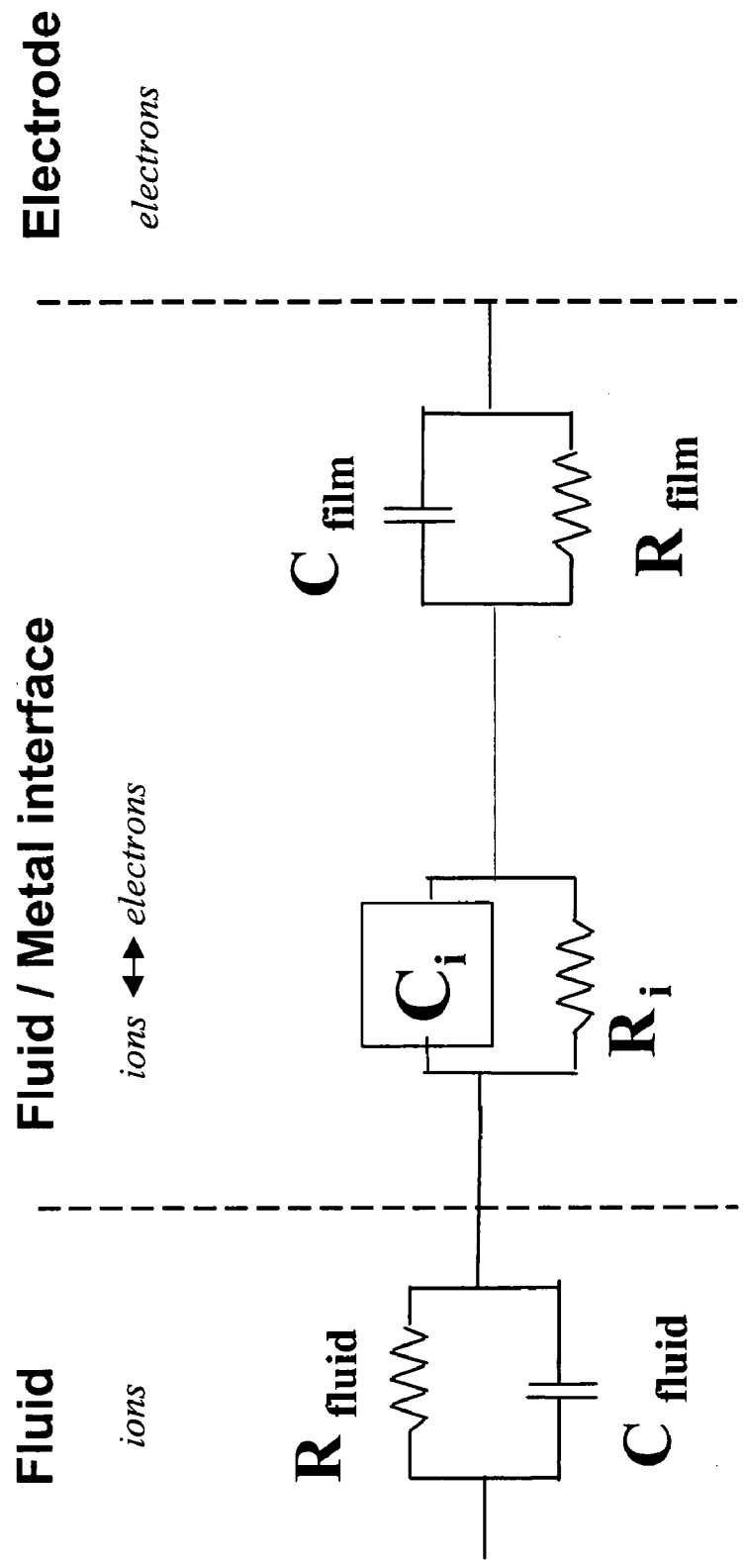
FIG. 11 is an illustration of a second alternative equivalent circuit for modeling impedance spectra data.

Equivalent circuit modeling of these IS data (FIGS. 9 and 10) shows that three IS parameter time constants are present for measurements beginning at and subsequent to one hour at temperature. The corresponding equivalent circuit model is illustrated in FIG. 11.

TABLE 3

Base Fluid Plus Secondary ZDDP, IS Parameters as a Function of Time at 120 Degrees Celsius

| TIME (hours) | $R_{fluid}$ (ohms) | $C_{fluid}$ (farads) | $\tau_{fluid}$ (sec) | $C_{film}$ (farads) | $R_{film}$ (ohms) | $\tau_{film}$ (sec) | $R_i$ (ohms) | $C_i$ (farads) | $\tau_i$ (sec) |
|---|---|---|---|---|---|---|---|---|---|
| 0.3 | $2.26 \times 10^8$ | $1.23 \times 10^{-10}$ | $2.07 \times 10^{-2}$ | not present | not present | not present | $1.52 \times 10^7$ | $2.27 \times 10^{-7}$ | 3.46 |
| 1.0 | $1.75 \times 10^8$ | $1.20 \times 10^{-10}$ | $2.06 \times 10^{-2}$ | $1.68 \times 10^{-8}$ | $1.41 \times 10^7$ | $2.37 \times 10^{-1}$ | $2.29 \times 10^7$ | $2.79 \times 10^{-8}$ | 1.33 |
| 2.0 | $1.24 \times 10^8$ | $1.16 \times 10^{-10}$ | $1.44 \times 10^{-2}$ | $2.76 \times 10^{-8}$ | $8.49 \times 10^6$ | $2.35 \times 10^{-1}$ | $3.49 \times 10^7$ | $2.72 \times 10^{-8}$ | 0.951 |
| 3.0 | $1.14 \times 10^8$ | $1.17 \times 10^{-10}$ | $1.32 \times 10^{-2}$ | $3.22 \times 10^{-8}$ | $6.74 \times 10^6$ | $2.17 \times 10^{-1}$ | $4.03 \times 10^7$ | $2.79 \times 10^{-8}$ | 1.12 |
| 4.0 | $1.19 \times 10^8$ | $1.17 \times 10^{-10}$ | $1.37 \times 10^{-2}$ | $3.29 \times 10^{-8}$ | $6.48 \times 10^6$ | $2.13 \times 10^{-1}$ | $3.99 \times 10^7$ | $2.96 \times 10^{-8}$ | 1.18 |
| 5.0 | $1.32 \times 10^8$ | $1.17 \times 10^{-10}$ | $1.54 \times 10^{-2}$ | $3.00 \times 10^{-8}$ | $6.80 \times 10^6$ | $2.04 \times 10^{-1}$ | $4.24 \times 10^7$ | $2.92 \times 10^{-8}$ | 1.24 |
| 6.0 | $1.44 \times 10^8$ | $1.23 \times 10^{-10}$ | $1.70 \times 10^{-2}$ | $2.98 \times 10^{-8}$ | $6.53 \times 10^6$ | $1.94 \times 10^{-1}$ | $4.25 \times 10^7$ | $4.71 \times 10^{-8}$ | 2.0 |

Figure 12:
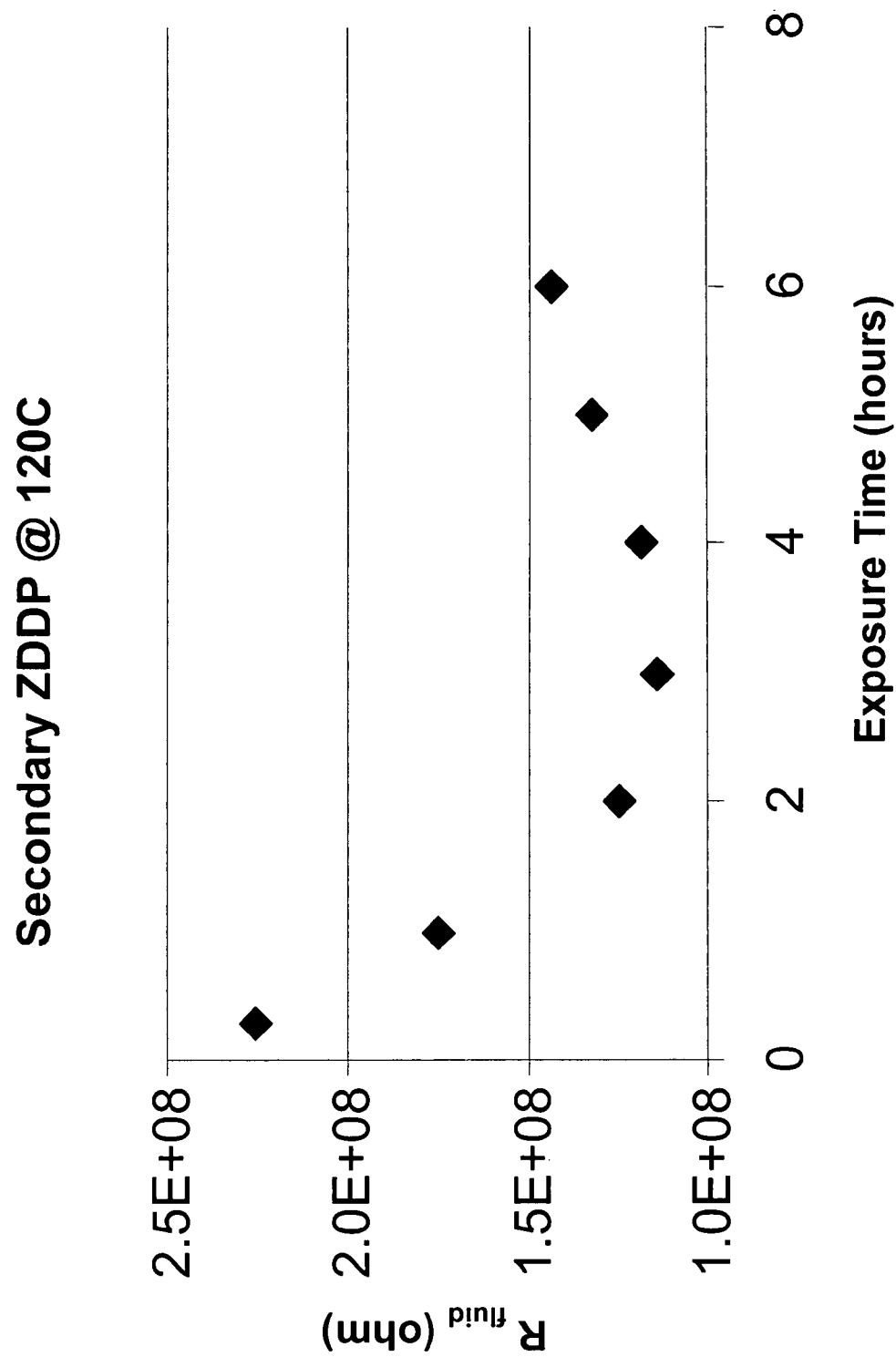
FIG. 12 is a plot of an equivalent circuit parameter $R_{fluid}$ versus time for thermal decomposition of a formulation including ZDDP.

The resistance $R_{fluid}$ (associated with bulk resistivity of the fluid) is shown as a function of time at temperature in FIG. 12, where the decrease from 0.3 to 3 hours, followed by an increase from 3.0 to 6.0 hours, as described above, is evident. The corresponding changes in bulk fluid capacitance $C_{fluid}$ are within a range of about 5% or less, as shown in TABLE 3 above. These exemplary results illustrate how the present inventive method may be used in determining changes in fluid properties (e.g., ion concentration and mobility) resulting from changes in formulation composition (e.g., chemical changes due to thermal decomposition).

Figure 13:
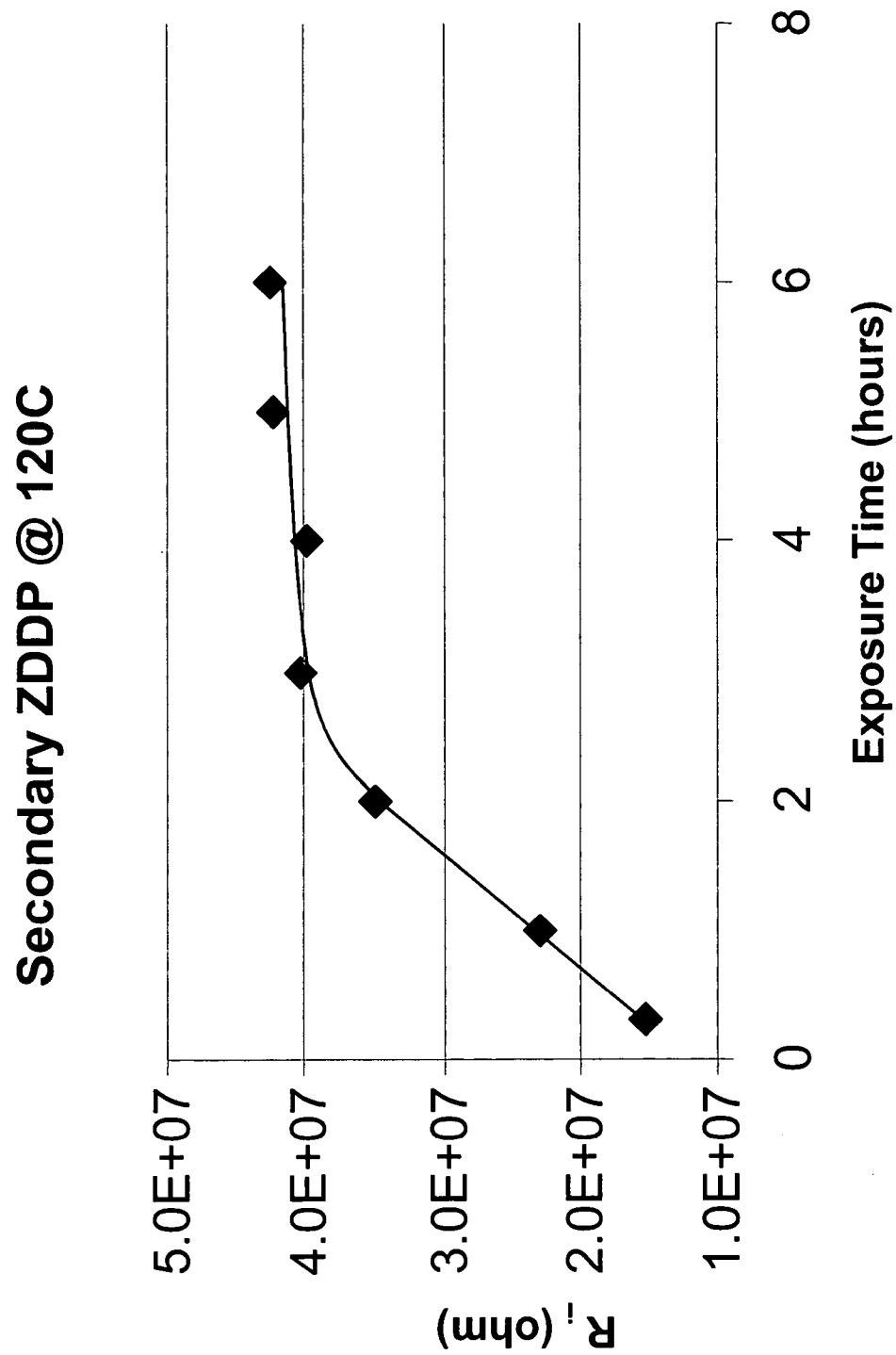
FIG. 13 is a plot of an equivalent circuit parameter $R_i$, versus time for thermal decomposition of a formulation including ZDDP.

FIG. 13 illustrates the interfacial resistance $R_i$ as a function of time at temperature. These data show a rapid increase for about 2 hours followed by a slower rate of increase beginning at about 3 hours. This behavior appears to reflect reactivity derived from adsorption that is governed by the concentration of surface active portion of the reactants in the fluid, which are decreasing with time due to oxidation or thermal decomposition. These exemplary results illustrate how the present inventive method may be used in determining changes in a fluid property (e.g., interface reactivity changes) resulting from changes in formulation composition (e.g., changes in concentration of reactants due to thermal decomposition).

Figure 14:
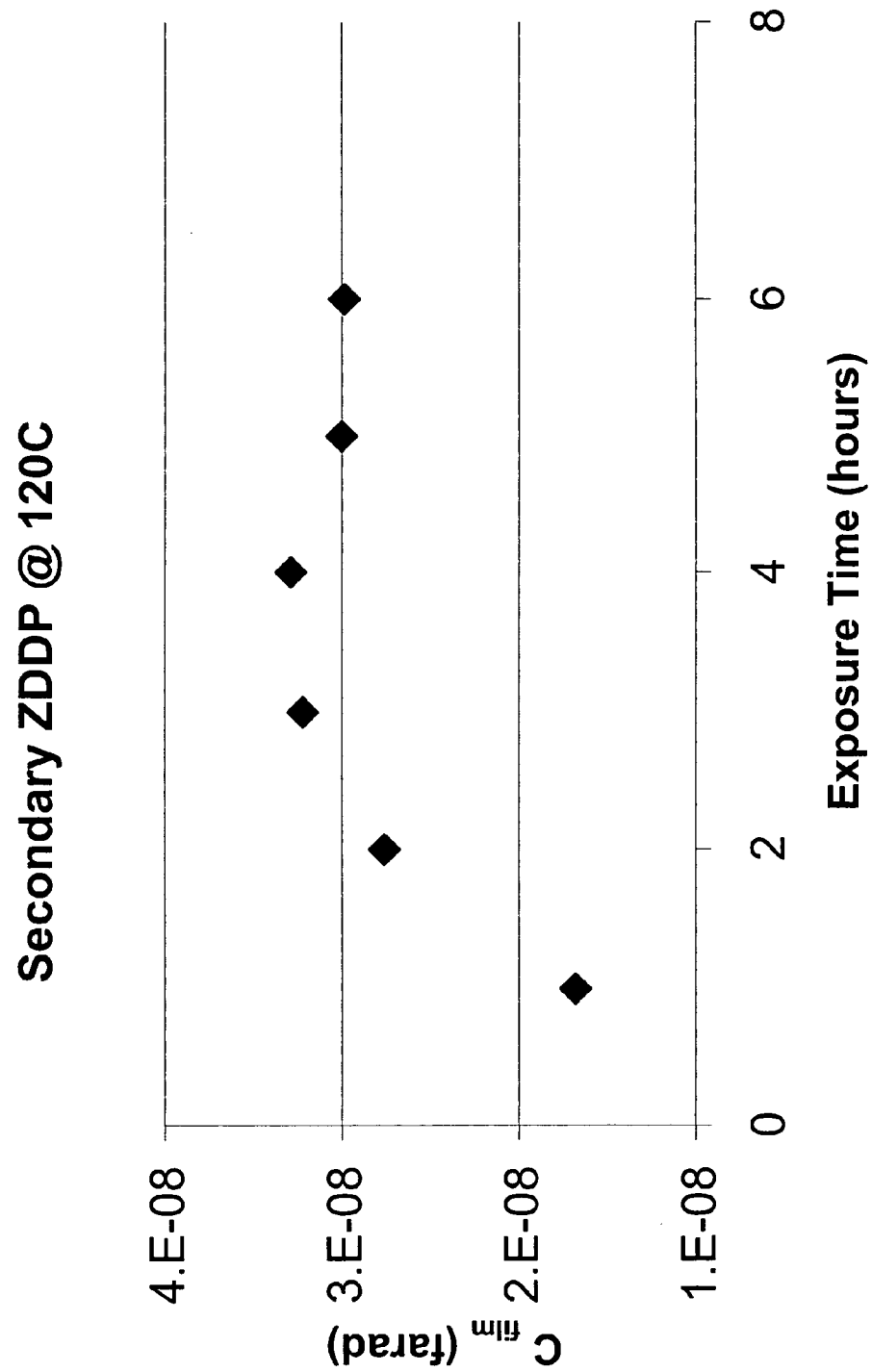
FIG. 14 is a plot of an equivalent circuit parameter $C_{film}$ versus time for thermal decomposition of a formulation including ZDDP.
Figure 15:
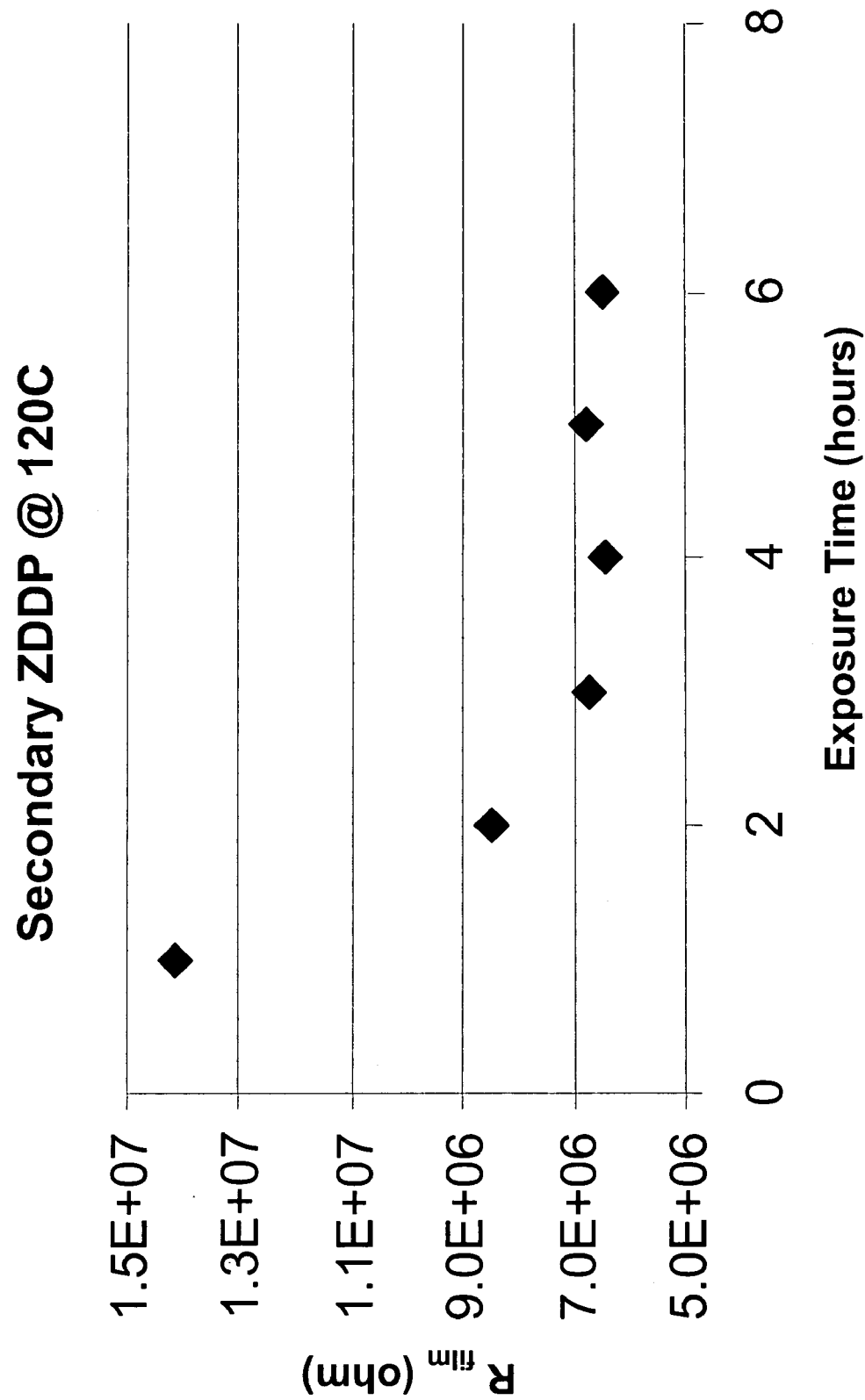
FIG. 15 is a plot of an equivalent circuit parameter $R_{film}$ versus time for thermal decomposition of a formulation including ZDDP.
Figure 16:
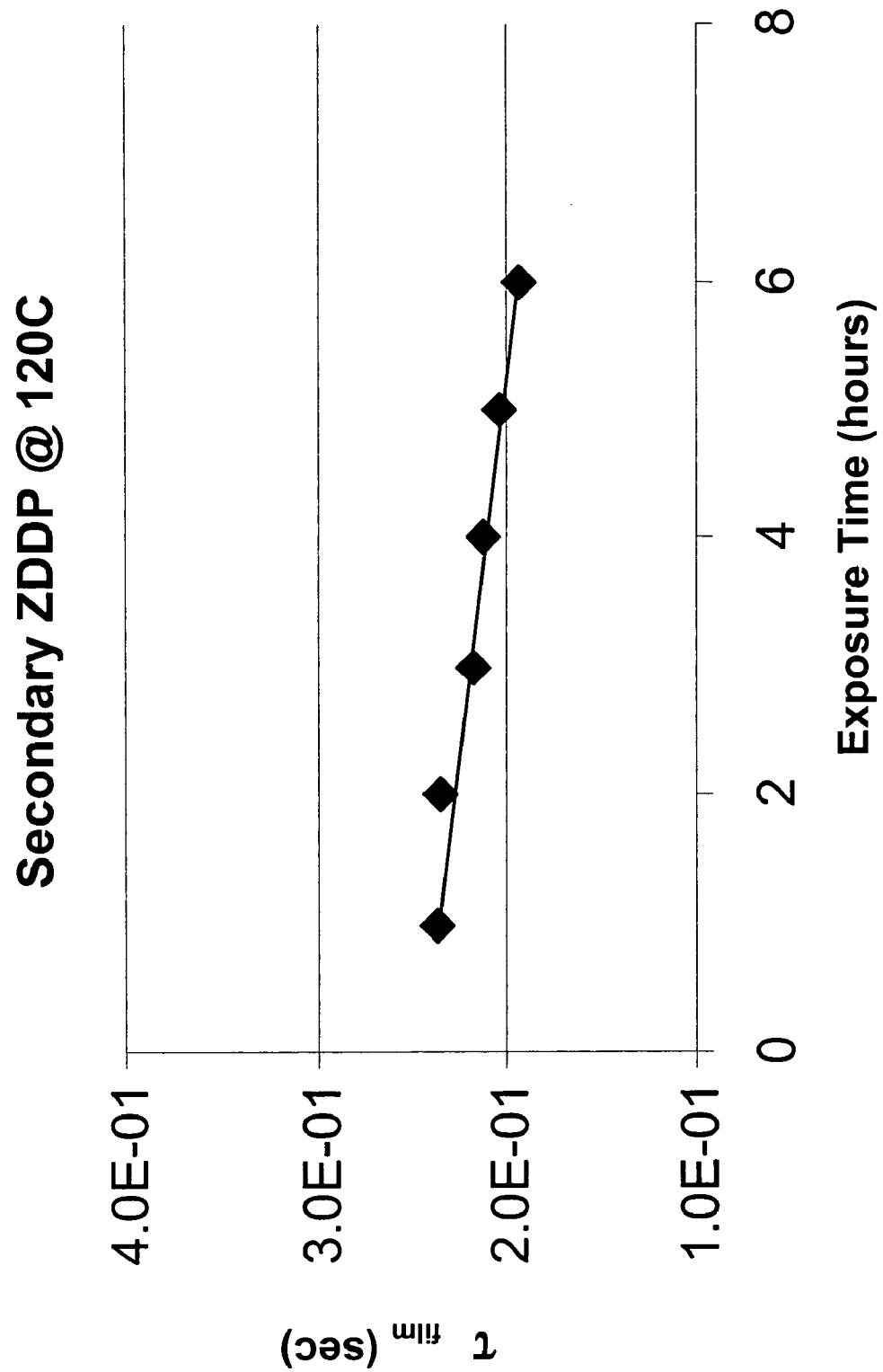
FIG. 16 is a plot of an equivalent circuit parameter $\tau_{film}$ versus time for thermal decomposition of a formulation including ZDDP.

While the time constants associated with the fluid itself and the reactivity at the metal surface are readily visible at the respective ends of the spectra (FIGS. 8 and 9), a third time constant is also detected after one hour of exposure. Although not prominent visually in the spectra, it is plausible that this parameter is derived from the presence/ formation of an adsorbed film. FIGS. 14, 15 and 16 illustrate the IS parameters relating to this fluid property as a function of exposure time.

The time dependence of the capacitance $C_{film}$ relating to the third time constant is shown in FIG. 14. In contrast, the resistance $R_{film}$ behaves in an inverse fashion, as illustrated in FIG. 15, suggesting that film geometry is undergoing a pronounced change during the first three hours of exposure. This appears to be indicative of film growth over a narrow area of coverage, followed by an increase in total coverage area as the generation of more species occurs. This progression would yield a film capacitance that is low initially (small area), and a resistance that is high also due to the reduced area. Broader area coverage over time would cause both values to increase and decrease, respectively, consistent with the observed behavior. Further, the film time constant $\tau_{film}$ values shown in FIG. 16 indicate that if this response is derived from a ZDDP-based film, it is not geometry alone that is changing. As the product of R and C yield a value that is geometry independent, the finite slope that is noted suggests that either the film resistivity and/or the polarizability also vary as exposure time increases. These exemplary results illustrate how the present inventive method may be used in determining changes in another fluid property (i.e., surface film formation) resulting from changes in formulation composition due to thermal decomposition.

EXAMPLE 4

Hot Oil Oxidation Test—Data Analysis Using Differential Impedance Parameter

In yet another embodiment of the present inventive concept, this example teaches novel IS parameters, and alternative methods for using data analyses in determining fluid and formulation properties. In particular, the present example teaches novel methods for determining changes in fluid properties during a Hot Oil Oxidation Test (HOOT).

The HOOT is a high-temperature (e.g., 160 degrees Celsius in this example) oxidation test that does not introduce combustion gasses into the fluids. The HOOT experiments described herein are performed in glass containers, thus the fluids are not exposed to metal during the oxidation process. There is also no mechanical fluid degradation such as may cause wear or mechanical shear. Fluid samples are removed from the oxidation vessel at periodic intervals and examined using both Fourier Transform Infra-Red (FTIR) spectroscopy and IS, to evaluate changes resulting from HOOT processing. HOOT oxidation is limited to the free radical, oxygen-sourced, oxidation pathways and thermal decompositions. The free radical pathways include production of alcohols, ketones, ester/lactones, and caboxylic acids. These oxidation mechanisms attack the base oil as a major pathway. They also attack the hydrocarbon chains of all of the additives. The presence of antioxidants gives additional decomposition pathways for the free radicals, and thus slows down the hydrocarbon oxidation.

Figure 17:
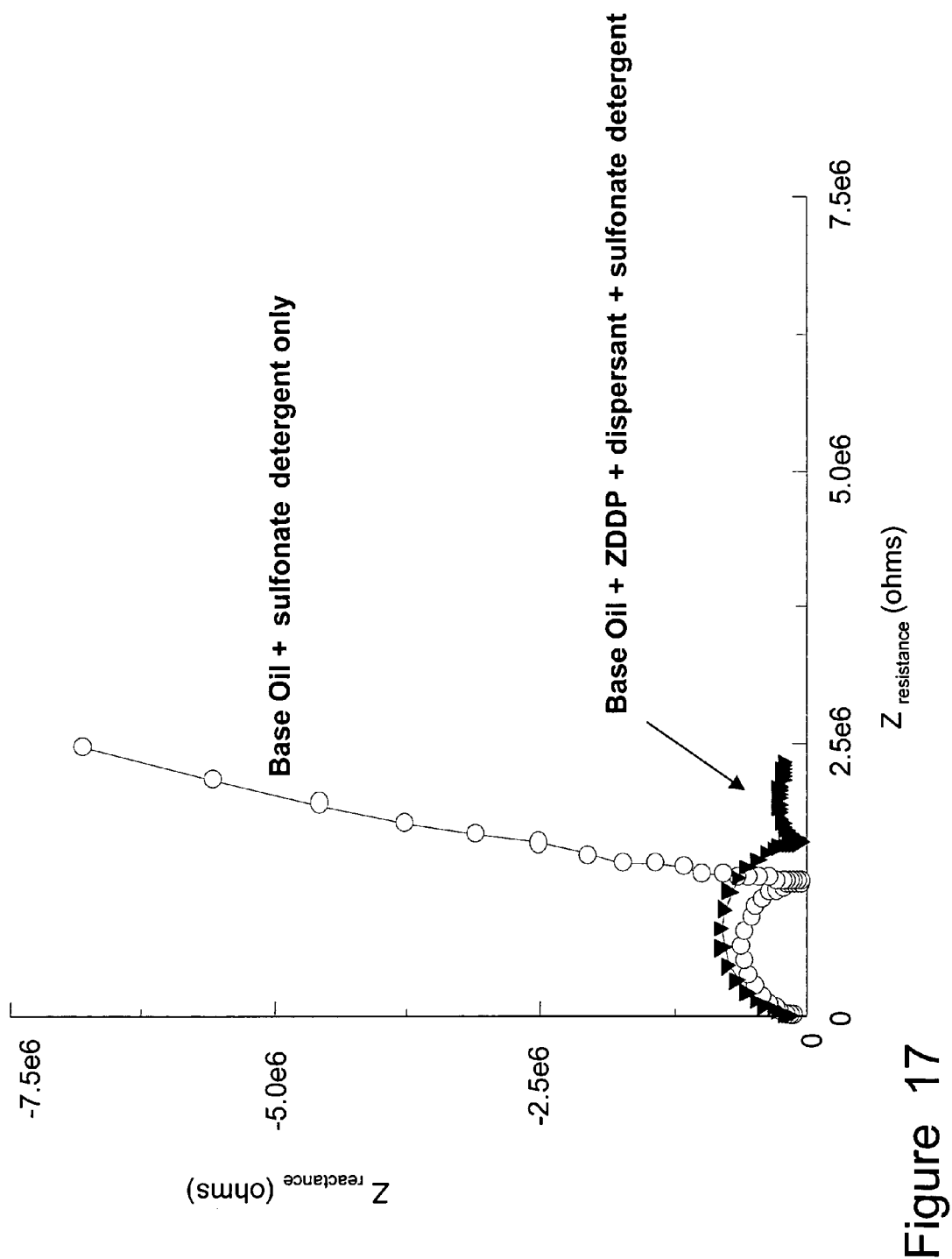
FIG. 17 is a plot of impedance spectroscopy data obtained for a first formulation comprising a base oil plus detergent and a second formulation comprising a base oil, ZDDP, a dispersant, and a detergent.

Two formulations are employed in this example. One formulation consists of a base oil plus a 3% concentration by weight of sulfonate detergent, and a second formulation consists of a base oil plus the following concentrations of additives by weight: 3% detergent, 1% ZDDP, and 6% dispersant. In these formulations, the base oil is a mildly hydrofinished 150 solvent neutral, hydrocarbon base stock. The ZDDP is a commercially available secondary ZDDP. The detergent is a commercially available highly overbased calcium alkylbenzene sulfonate. The dispersant is a commercially available succinimide type dispersant. These formulations are referred to herein as the detergent-only formulation and the ternary formulation, respectively. Both formulations are "partial" formulations in that they do not include the full range of additives typically found in final product lubricants. FIG. 17 illustrates the IS data for the formulations prior to the HOOT. These data indicate that the combined presence of all three additives, and interaction among these species, can be observed using broad spectrum IS measurements.

Figure 18:
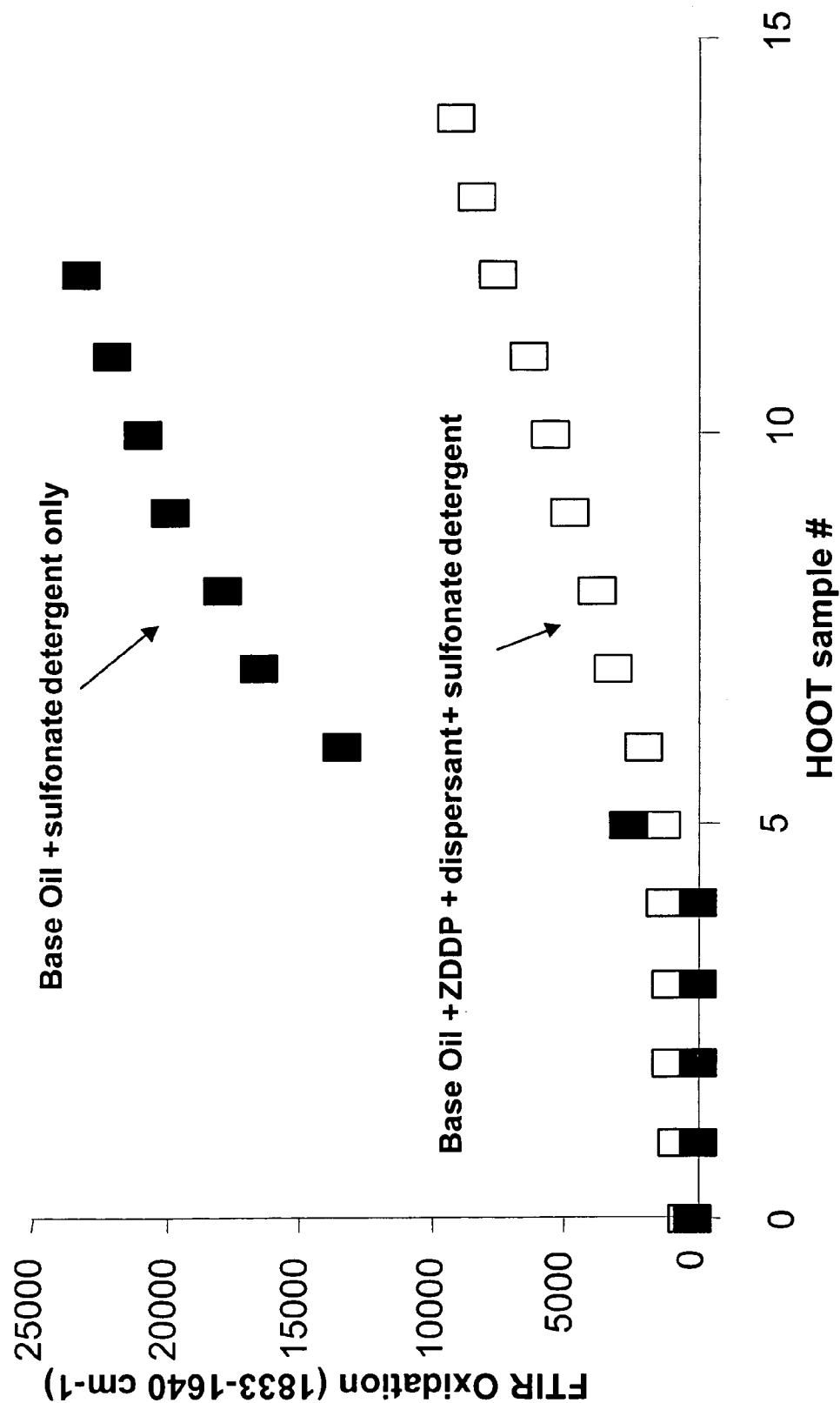
FIG. 18 is a time-dependent plot of FTIR oxidation data at 1833–1640 inverse-cm obtained from an oxidation test for a first formulation comprising a base oil plus detergent and a second formulation comprising a base oil, ZDDP, a dispersant, and a detergent.
Figure 19:
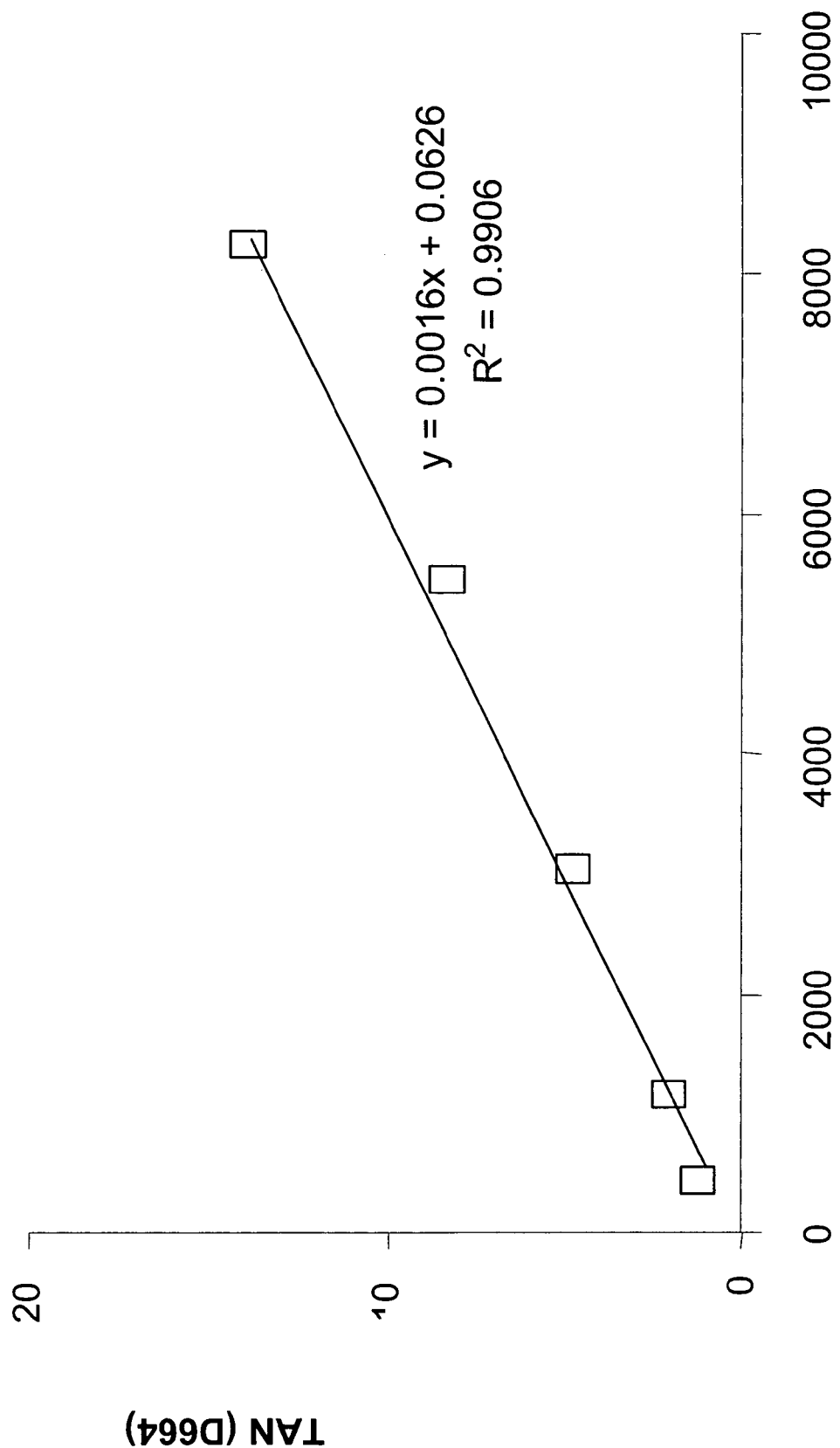
FIG. 19 is a plot of Total Acid Number (TAN) data versus FTIR oxidation data at 1833–1640 inverse-cm for a formulation consisting of a base oil, ZDDP, a dispersant, and a detergent.

FIG. 18 shows a plot of FTIR peak area calculations over the range of 1833–1640 $cm^{-1}$ (obtained by methods well known to persons skilled in the arts of FTIR measurements and analysis) versus HOOT process time, for the two formulations. The FTIR peak area calculation for 1833–1640 $cm^{-1}$ is a well known indication or metric of the oxidation process (also referred to herein by the equivalent terms "FTIR oxidation", "total oxidation", and "total carbonyl") in a lubricant. As noted above, the HOOT subjects the formulations to a temperature of 160 degrees Celsius, and samples are removed from the HOOT container at intervals for FTIR and IS measurements, performed at 80 degrees Celsius. The 15 sample numbers, 0 to 14, shown in the FIG. 18 span an interval range of 145 hours. The sample numbers 0 through 14 correspond to the following sample times: 0 hours, 1 hour, 2 hours, 3 hours, 6 hours, 8.5 hours, 18 hours, 24 hours, 31.5 hours, 44 hours, 55.5 hours, 72.5 hours, 96 hours, 120.5 hours, and 145 hours, respectively. The data of FIG. 18 reveal that significantly lower total oxidation results for the ternary formulation than for the detergent-only formulation. Due to the aromatic portion of this additive, and its sulfonate polar head group, the detergent additive is a pro-oxidant. As shown in FIG. 19, these total oxidation values correlate well with the increase in Total Acid Number per ASTM D664, which is an alternative method, well known to persons skilled in the arts of petroleum engineering, of 2 0 measuring the degree of lubricant total oxidation. The data points shown in the FIG. 19 correspond, from left to right, to the sample numbers 1, 3, 7, 10, and 14, respectively.

Figure 20:
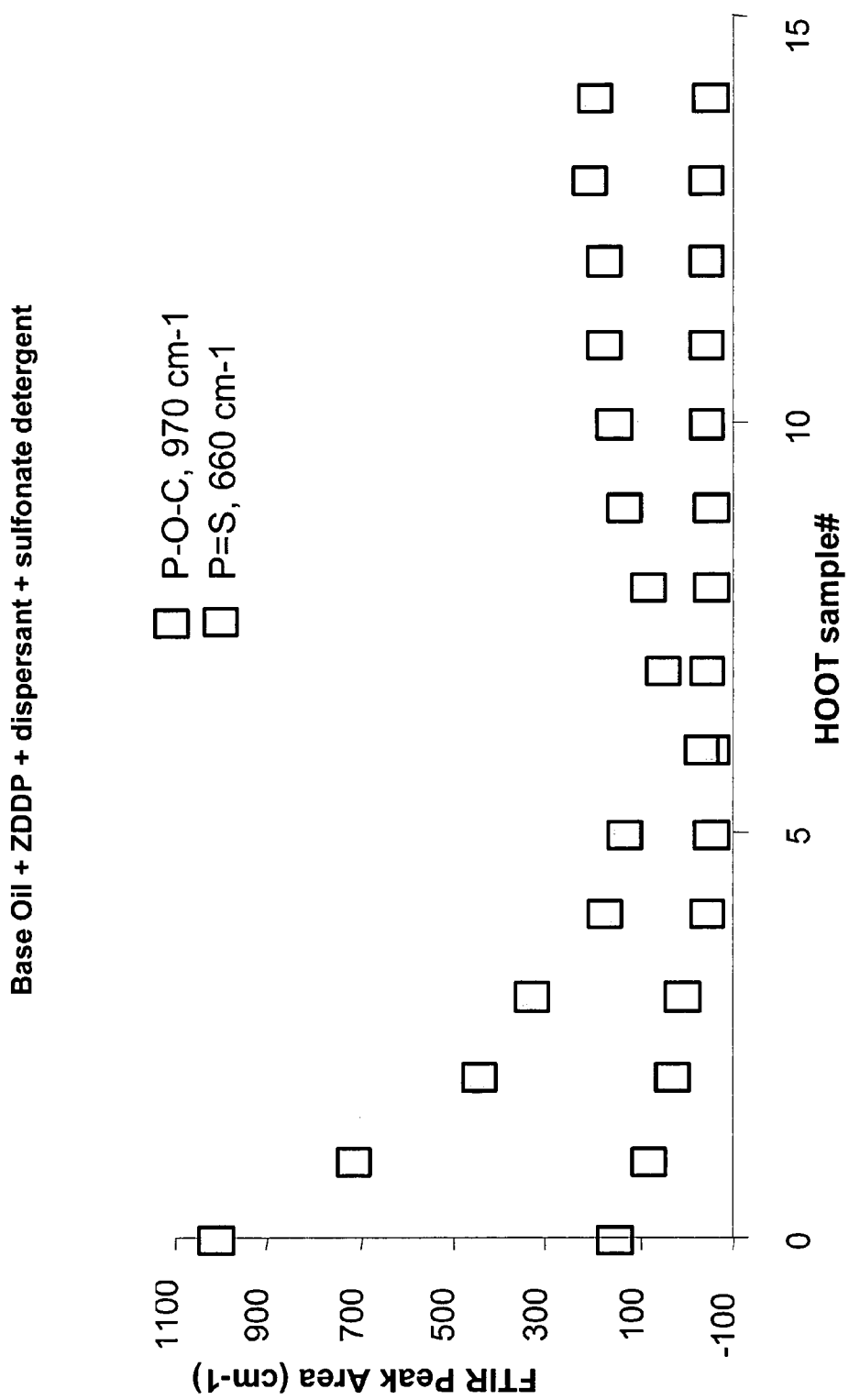
FIG. 20 is a plot of FTIR Peak Area data at 660 and 970 inverse-cm versus Hot Oil Oxidation Test (HOOT) sample number, obtained for a formulation consisting of a base oil, ZDDP, a dispersant, and a detergent.
Figure 21:
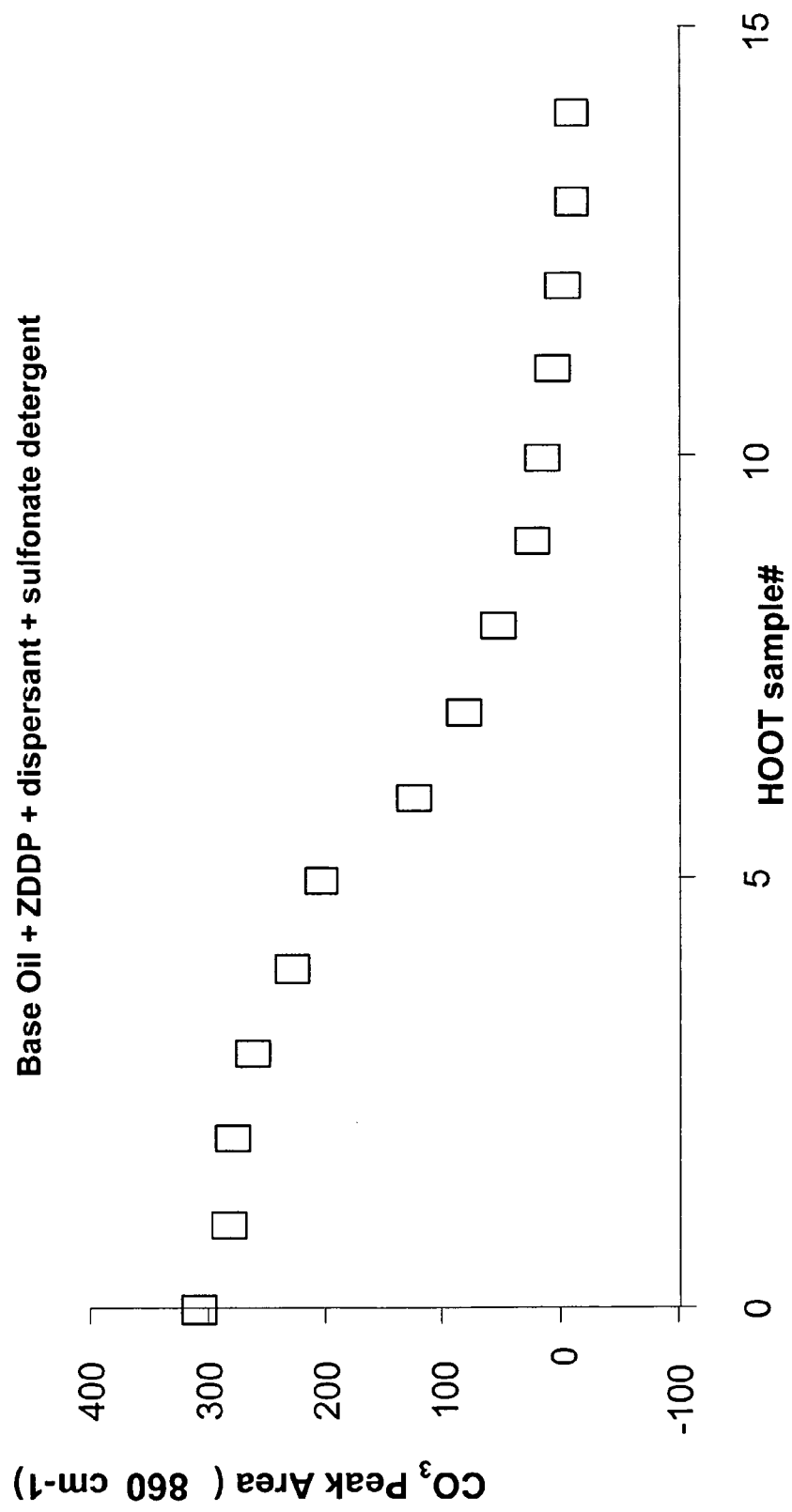
FIG. 21 is a plot of $CO_3$ Peak Area FTIR data at 860 inverse-cm (cm-1) versus Hot Oil Oxidation Test sample number, obtained for a formulation consisting of a base oil, ZDDP, a dispersant, and a detergent.

In addition to oxidation products, the presence of a ZDDP concentration in the fluid is characterized via FTIR peak area calculations at 645 $cm^{-1}$ (indicative of P=S bond concentration) and 970 $cm^{-1}$ (indicative of P—O—C bond concentration), as illustrated in FIG. 20. During decomposition of this additive, non-ionic intermediates are produced, which further decompose into ionic products. The final decomposition product is zinc phosphate or pyro-phosphate, which has poor solubility in the oil matrix. As the free radicals are formed, the ZDDP quenches them, and prevents the hydrocarbon oxidation. The calcium carbonate forms salts with the oxidized acids, yielding the carbonate concentration depletion (via FTIR data at 860 $cm^{-1}$) as a function of ongoing fluid sampling, as shown in FIG. 21.

Figure 22:
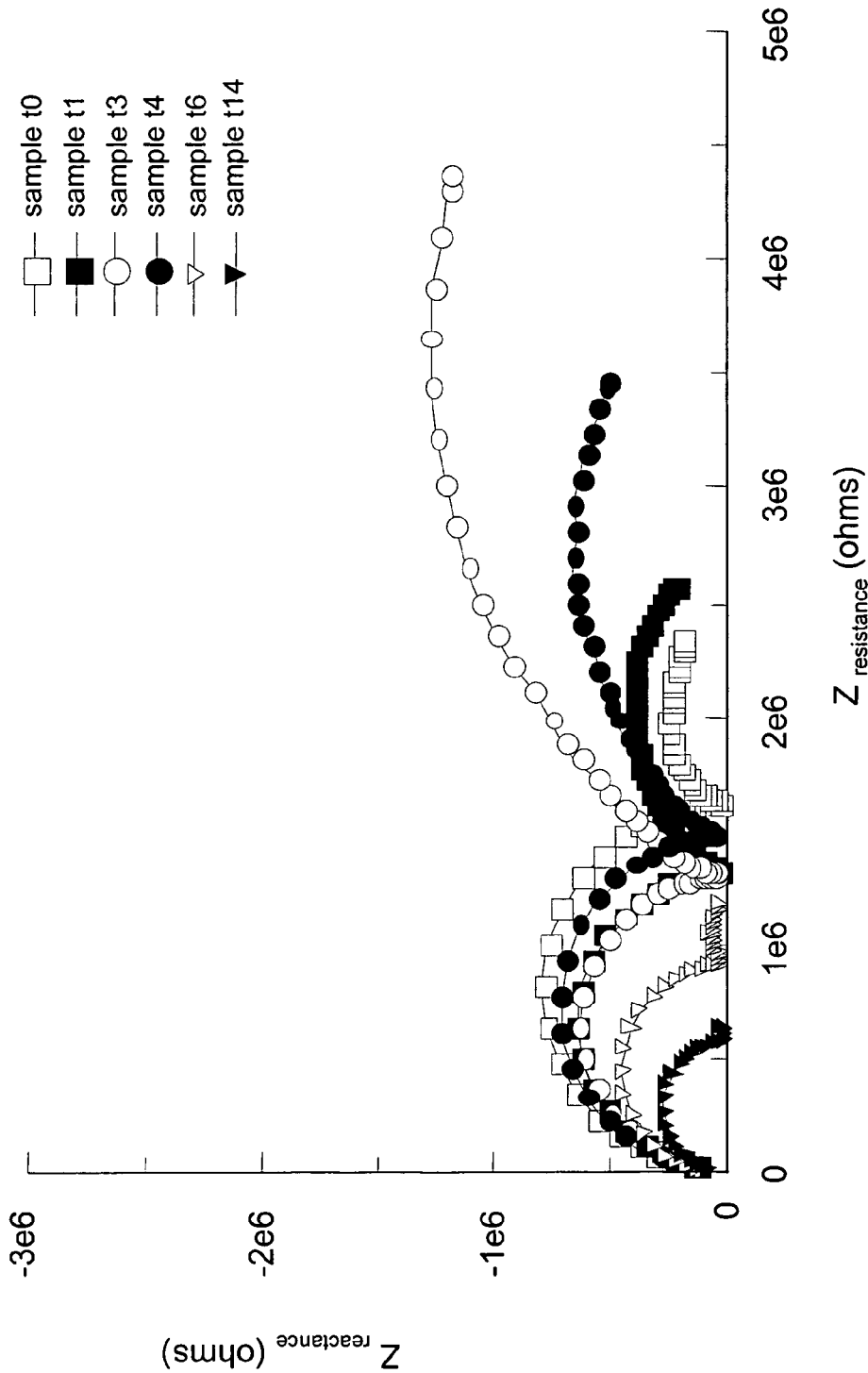
FIG. 22 shows a plurality of plots of impedance spectroscopy data, each plot representing a selected Hot Oil Oxidation Test process time, obtained for a formulation consisting of a base oil, ZDDP, a dispersant, and a detergent.

FIG. 22 shows exemplary IS data at 80 degrees Celsius obtained for the ternary formulation, as measured after cumulative HOOT exposure intervals for the sample numbers 0, 1, 3, 4, 6 and 14. These spectra exhibit a bi-directional behavior (i.e., the magnitude of the impedances first increase, and then subsequently decrease) as a function of HOOT time.

Figure 23:
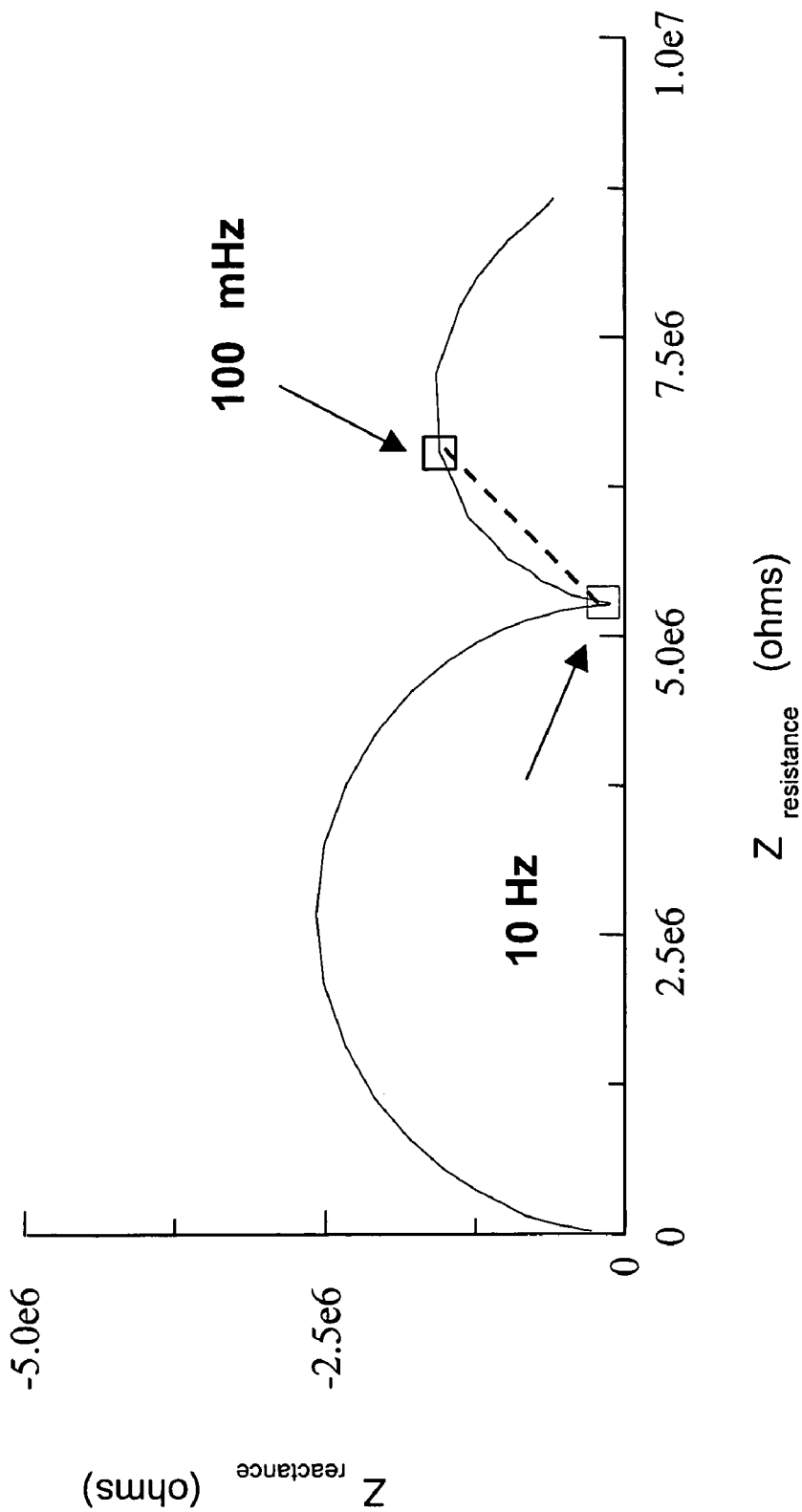
FIG. 23 is a plot of exemplary impedance spectroscopy data illustrating evaluation points for a differential impedance parameter.

FIG. 23 illustrates an IS parameter that may be correlated to the chemical changes in the fluid properties described above in reference to FIGS. 18, 19, 20 and 21. As illustrated in FIG. 23, an interface impedance difference (termed "dZmaglow") may be calculated for two frequencies that are selected to reduce the influence of bulk impedance changes on the data analyses. For the present example, dZmaglow may be defined in accordance with the following equation:

$$dZmaglow = SQRT[(Z_{resistance @ 100\ mHz} - Z_{resistance @ 10\ Hz})^2 + (Z_{reactance @ 100\ mHz} - Z_{reactance @ 10\ Hz})^2].$$

Figure 24:
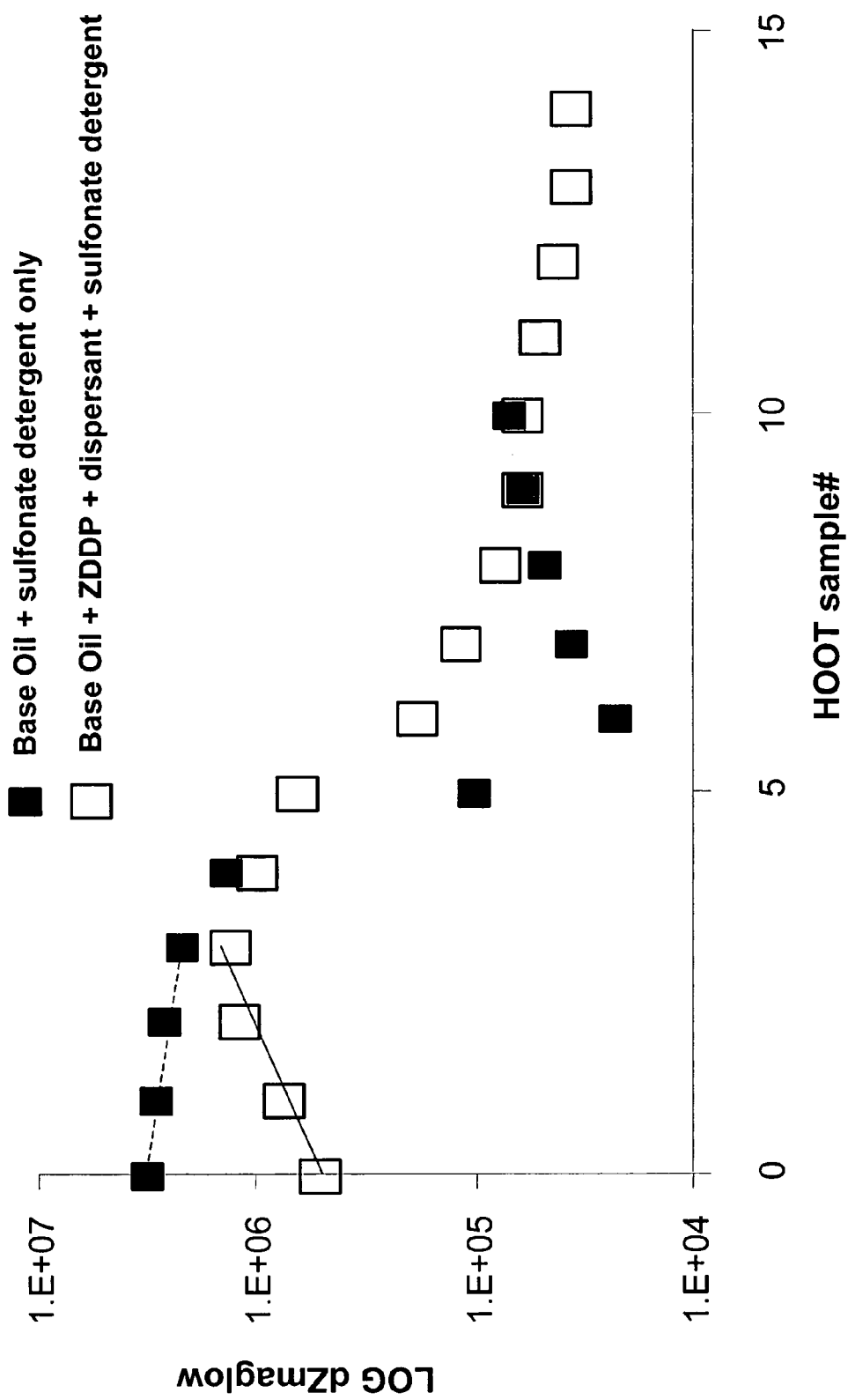
FIG. 24 is a plot of a differential impedance parameter LOG dZmaglow versus Hot Oil Oxidation Test sample number, obtained for a first formulation consisting of a base oil plus detergent and a second formulation consisting of a base oil, ZDDP, a dispersant, and a detergent.

For these exemplary isothermal data, the Nyquist minimum occurs close to 10 Hz. For a more general case, the definition of dZmaglow may employ selected frequencies wherein the higher frequency is close to the Nyquist minimum, and the lower frequency may be selected to be at least a factor of 10 below the higher frequency. The IS difference parameter dZmaglow is an interfacial impedance parameter that is indicative of the relative interface reactivity of electro-active species at the metal electrode surface (i.e., an exemplary fluid property), and provides a novel and advantageous means for observing related changes in formulation properties such as total oxidation products, ZDDP concentration, carbonate depletion, etc. As will be shown in TABLES 4 and 5 below, other exemplary IS difference parameters (e.g., dZmaghigh, dZmagmid, and dZmagverylow) may also be defined and implemented. In FIG. 24, plots of the dZmaglow parameter versus HOOT sample number for the detergent-only formulation and the ternary formulation are shown. The data exhibit bi-directional impedance changes that differ markedly between the different fluids. These data are indicative of the different chemical processes that occur in the two formulations when exposed to the HOOT process, and illustrate how the IS difference parameter dZmaglow can be used to distinguish between the chemical properties of the two formulations.

Figure 25:
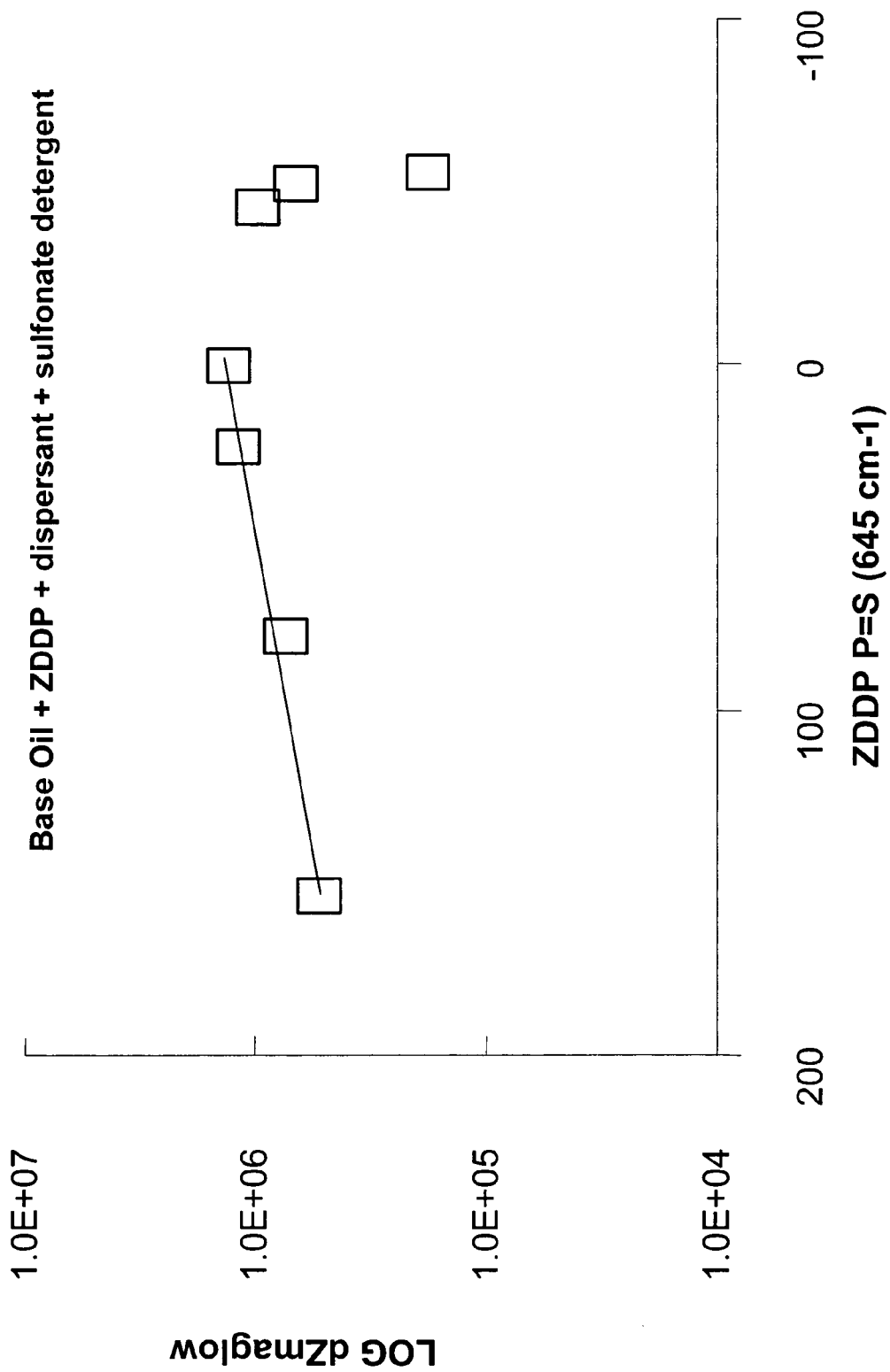
FIG. 25 is a plot of a differential impedance parameter LOG dZmaglow versus FTIR data at 645 inverse-cm, obtained for selected samples from a Hot Oil Oxidation Test sequence, for a formulation consisting of a base oil, ZDDP, a dispersant, and a detergent.
Figure 26:
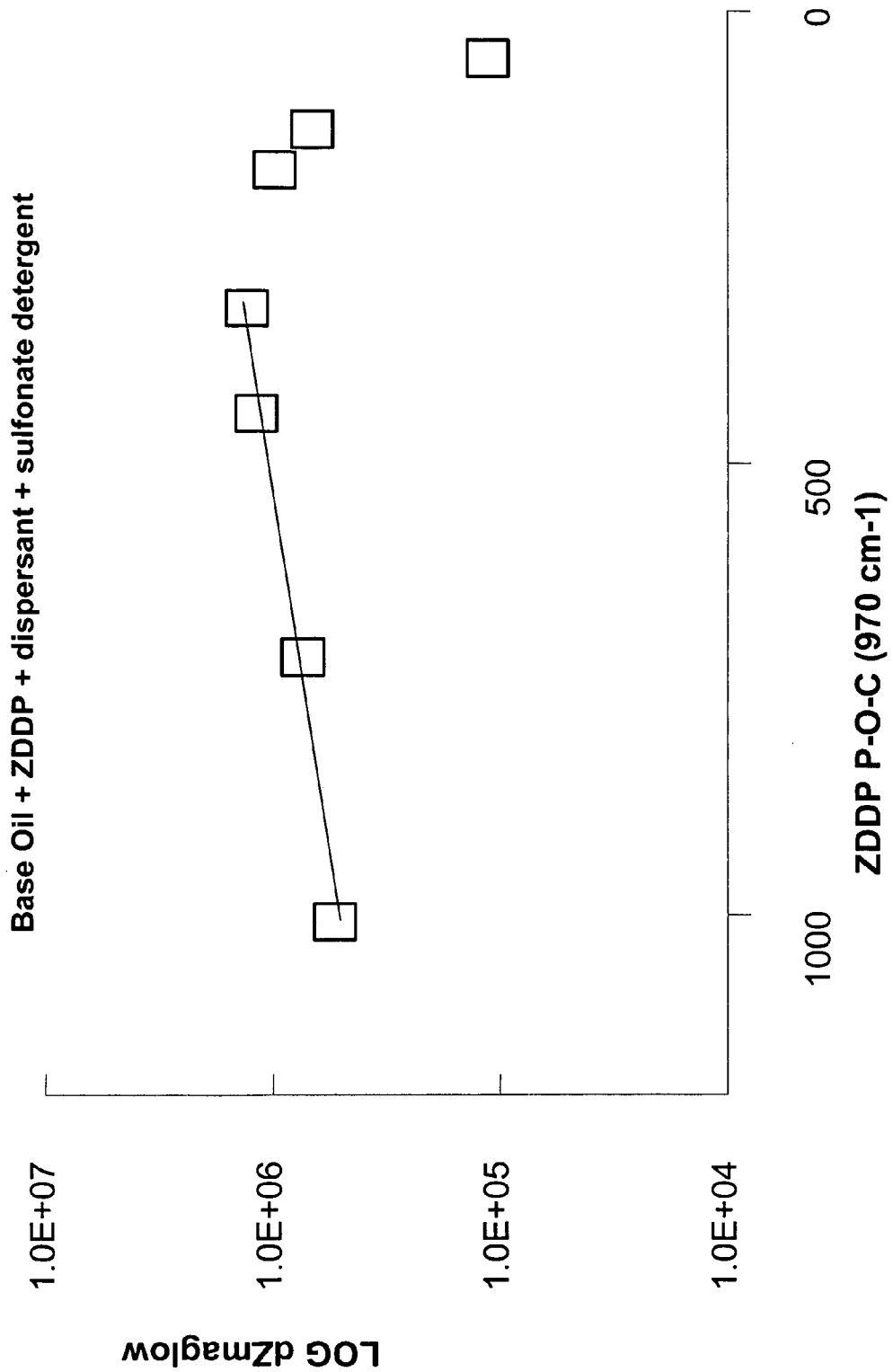
FIG. 26 is a plot of a differential impedance parameter LOG dZmaglow versus FTIR data at 970 inverse-cm, obtained for selected samples from a Hot Oil Oxidation Test sequence, for a formulation consisting of a base oil, ZDDP, a dispersant, and a detergent.
Figure 27:
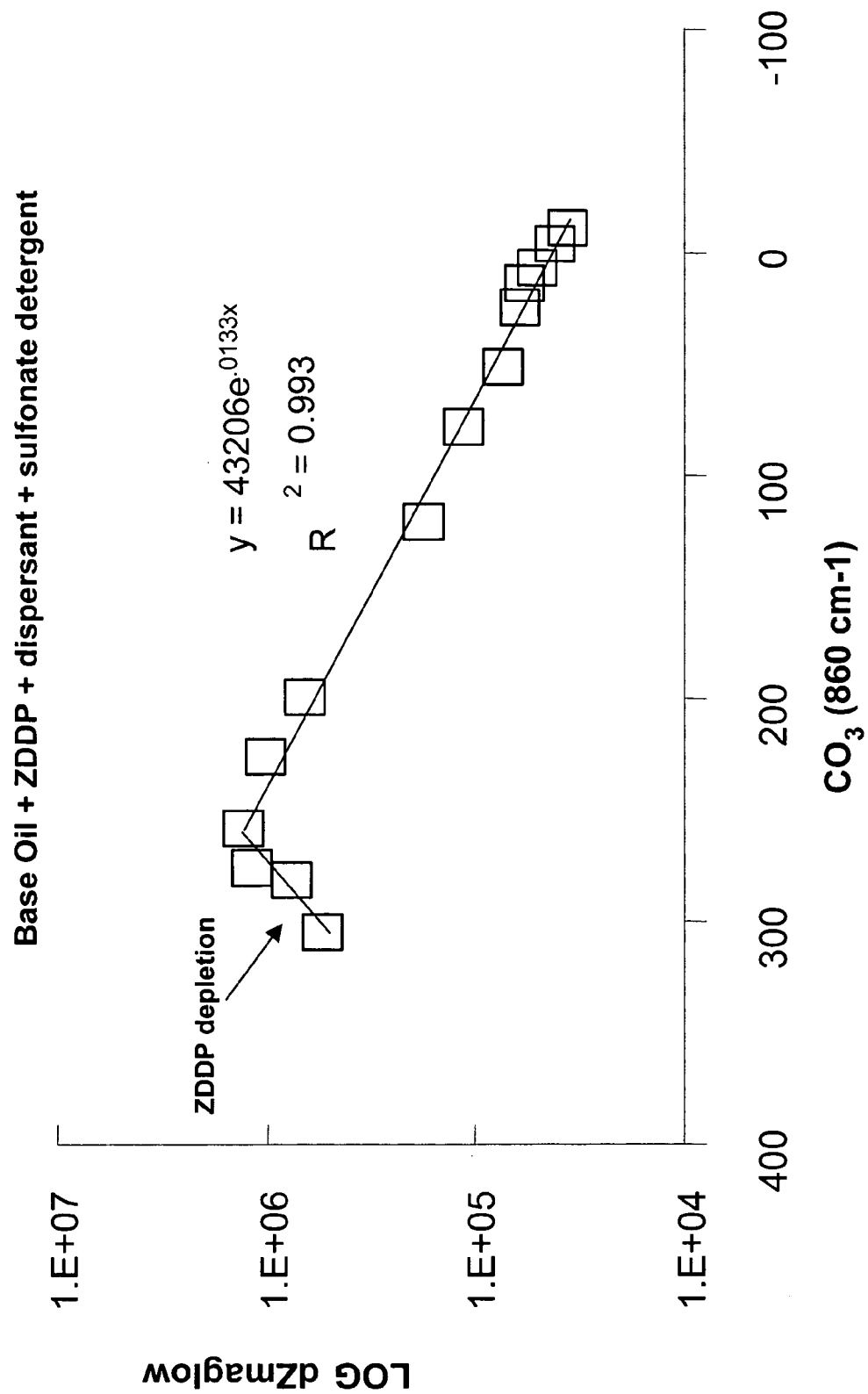
FIG. 27 is a plot of a differential impedance parameter LOG dZmaglow versus FTIR data at 860 inverse-cm, obtained for selected samples from a Hot Oil Oxidation Test sequence, for a formulation consisting of a base oil, ZDDP, a dispersant, and a detergent.
Figure 28:
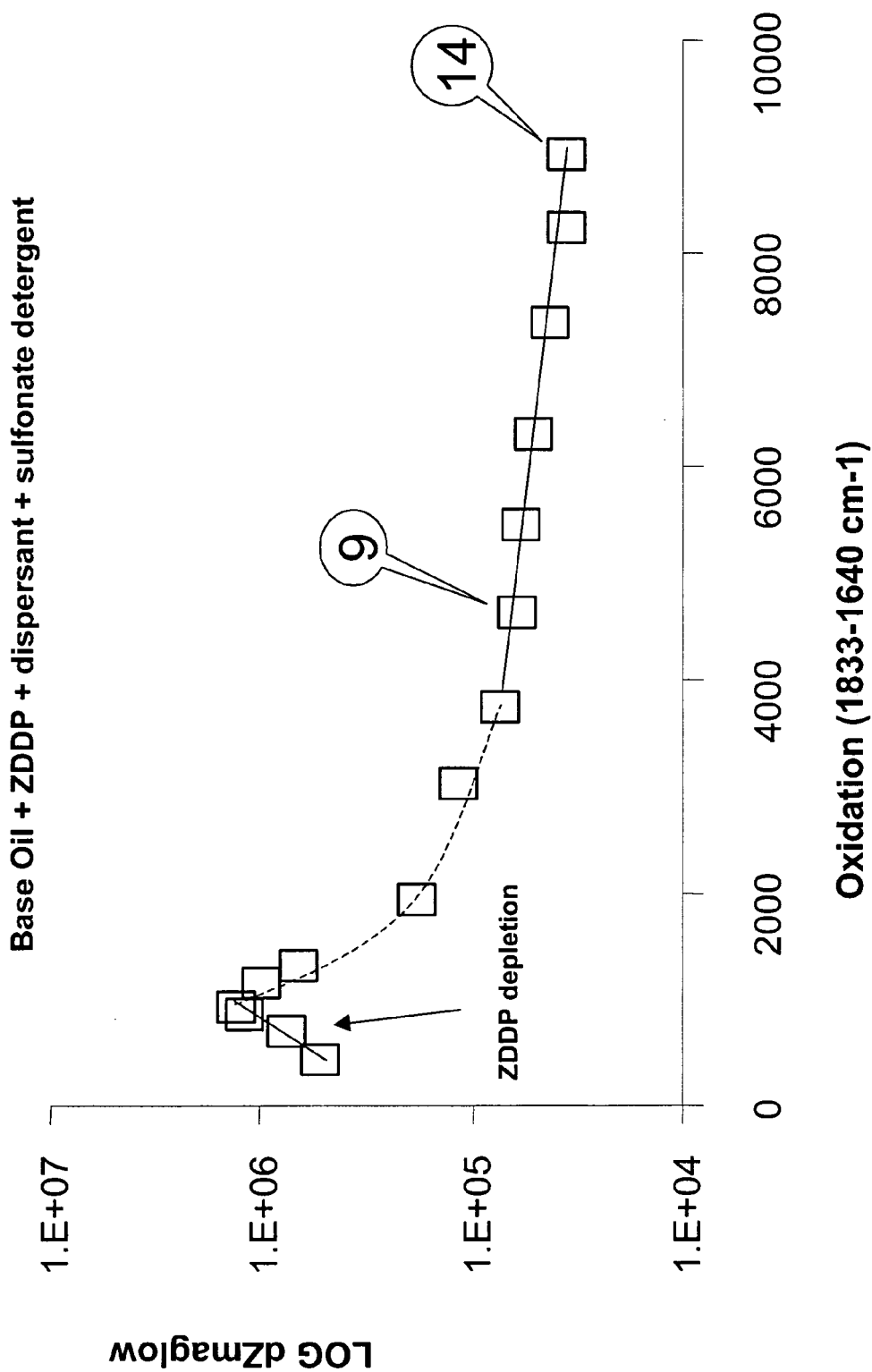
FIG. 28 is a plot of a differential impedance parameter LOG dZmaglow versus FTIR oxidation data at 1833–1640 inverse-cm, obtained for selected samples from a Hot Oil Oxidation Test sequence, for a formulation consisting of a base oil, ZDDP, a dispersant, and a detergent.

In the early stage of HOOT processing of the ternary formulation, the IS difference parameter dZmaglow increases as ZDDP decomposition (both P=S and P—O—C bonds) is detected by FTIR. This correlation is shown in FIGS. 25 and 26, and occurs prior to substantial increases in total oxidation as also determined by FTIR. The data points shown in the FIGS. 25 and 26 correspond, from left to right, to sample numbers 0, 1, 2, 3, 4, 5 and 6, respectively. It is observed that the IS difference parameter dZmaglow subsequently decreases as $CO_3$ concentration depletion ensues, as shown in FIG. 27, coincident with the onset of oxidation. After the $CO_3$ is depleted at later HOOT process times, the decrease in dZmaglow indicates increased interface reactivity that is related to oxidation products, as seen in FIG. 28 by the decrease in dZmaglow occurring between samples 9 and 14 indicated by the callouts. The data points shown in the FIGS. 27 and 28 correspond, from left to right, to sample numbers 0 to 14, respectively. For FIG. 27, the data points for sample numbers 13 and 14 are coincident and indistinguishable.

The teachings according to this example show the use of an IS difference parameter (e.g., dZmaglow) to determine exemplary fluid properties (i.e., total oxidation, P=S bond concentration, P—O—C bond concentration, ZDDP concentration, $CO_3$ concentration, etc.) relating to changes in formulation composition changes (i.e., additive depletion and the generation of oxidation products in a formulation) during HOOT processing.

EXAMPLE 5

Hot Oil Oxidation Test—Data Analysis Using Statistical Techniques

In the description below, another embodiment of the present inventive concept is set forth, wherein a plurality of IS parameters are analyzed in combination using statistical techniques. As noted above, exemplary statistical techniques include, without limitation, Principal Component Analysis (PCA), Multivariate Least Squares Regression (MLR), Principal Component Regression (PCR), Group Method for Data Handling (GMDH), Pattern Recognition analysis, Cluster analysis, and Neural Net analysis. A description of these techniques in reference to IS data analysis is disclosed in the co-pending U.S. Patent Application, application Ser. No. 10/723,624, filed Nov. 26, 2003, titled "FLUID CONDITION MONITORING USING BROAD SPECTRUM IMPEDANCE SPECTROSCOPY". This above-incorporated application is set forth in full in Appendix A of the present application.

To apply the GMDH technique, a more extensive list of possible IS parameters is developed to include both raw data extractions and derived calculations. These exemplary IS parameters are summarized in a TABLE 4 shown below.

TABLE 4

Exemplary IS Parameters for Statistical Analysis zreal10kHz
zimag10kHz
zreal100Hz
zimag100Hz
zreal10Hz
zimag10Hz
zreal100mHz
zimag100mHz
zreal10mHz
zimag10mHz
invzreal10kHz=1/zreal10kHz;
invzimag10kHz=1/zimag10kHz;
invzreal100Hz=1/zreal100Hz;
invzimag100Hz=1/zimag100Hz;
invzreal10Hz=1/zreal10Hz;
invzimag10Hz=1/zimag10Hz;
invzreal100mHz=1/zreal100mHz;
invzimag100mHz=1/zimag100mHz;
invzreal10mHz=1/zreal10mHz;
invzimag10mHz=1/zimag10mHz;
TANDhigh=(zreal10Hz/zimag10Hz);
TANDlow=(zreal100mHz/zimag100mHz);
TANDvlow=(zreal10mHz/zimag10mHz);
dZmaghigh=(((zreal100mHz-zreal100Hz)^2)+((zimag100mHz-zimag100Hz)^2))^.5;
dZmaglow=(((zreal100mHz-zreal10Hz)^2)+((zimag100mHz-zimag10Hz)^2))^.5;
dZmagmid=(((zreal10mHz-zreal10Hz)^2)+((zimag10mHz-zimag10Hz)^2))^.5;
dZmagverylow=(((zreal10mHz-zreal100mHz)^2)+((zimag10mHz-zimag100mHz)^2))^.5;
Angle1=Re[ArcSin[-1 *(zimag100mHz-zimag100Hz)/dZmaghigh]* 180/Pi];
Angle2=Re[ArcSin[-1 *(zimag100mHz-zimag10Hz)/dZmaglow]* 180/Pi];
Angle3=Re[ArcSin[-1 *(zimag10mHz-zimag100mHz)/dZmagverylow]* 180/Pi]

The selection of the IS parameters shown in the TABLE 4 will be readily understood by persons skilled in the arts of computer science and statistical analysis. For example, zreal10 kHz, zreal100 Hz, zreal10 Hz, zreal100 mHz, zreal10 mHz, represent the resistive parts of the complex impedance Z evaluated at 10 kHz, 100 Hz, 100 mHz, and 10 mHz, respectively. Similarly, zimag10 kHz, zimag100 Hz, zimag10 Hz, zimag100 mHz, zimag 10 mHz, represent the reactive part of the complex impedance Z evaluated at 10 kHz, 100 Hz, 100 mHz, and 10 mHz, respectively. These evaluation frequencies are appropriate for the exemplary data disclosed herein. Other IS parameters are defined by the equations as shown in the TABLE 4.

Other evaluation frequencies may also be used for the IS parameters of TABLE 4, in accordance the present inventive concept, as persons skilled in the arts of data analysis will readily understand from the teachings herein. Expressed in terms of generalized evaluation frequencies $f_m$, $f1_n$ and $f2_n$, the IS parameters listed in TABLE 4 may be represented in a generalized form as follows: zreal($f_m$), zimag($f_m$), invzreal($f_m$), invzimag($f_m$), TAND($f_m$), dZmag($f1_n$, $f2_n$) and ANGLE ($f1_n$, $f2_n$);

where m and n are positive integers indexing the distinct frequencies for which specific instances of each parameter are evaluated;

where the generalized IS parameter invzreal($f_m$)=1/zreal ($f_m$);

where the generalized IS parameter invzimag($f_m$)=1/zimag ($f_m$);

where the generalized IS parameter TAND($f_m$)=zreal($f_m$)/zimag($f_m$), represents one or more IS parameters as exemplified by TANDhigh, TANDlow, and TANDvlow;

where the generalized IS parameter dZmag($f1_n$, $f2_n$)={[zreal($f1_n$)−zreal($f2_n$)]$^2$ +[zimag($f1_n$)−zimag($f2_n$)]$^2$}$^{1/2}$, represents one or more IS parameters as exemplified by dzmaghigh, dZmaglow, dzmagmid, and dzmagverylow; and where the generalized IS parameter ANGLE($f1_n$, $f2_n$) =Re{ArcSin[−1*(zimag($f1_n$)−zimag($f2_n$))/dZmag($f1_n$, $f2_n$)]*180/π}, represents one or more IS parameters as exemplified by Angle1, Angle2 and Angle3. The generalized frequencies $f_m$, $f1_n$ and $f2_n$ are chosen from within the frequency range of the IS measurements, and $f1_n \neq f2_n$. Typically, at least one value for $f1_n$ or $f2_n$ may be selected to correspond to the Nyquist minimum, as exemplified by dZmaglow. The IS parameters exemplified in TABLE 4, and the generalized forms of these IS parameters defined above, are equivalently referred to herein as "statistical IS parameters."

In addition to analyzing data for the ternary formulation described above, GMDH calculations are also performed for data obtained for two sets of HOOT processed fluid samples containing additional components. These new fluids consists of the ternary combination described above plus: a) 1% phenate detergent; and, b) 1% phenate detergent and 1% viscosity index improver. The data analyses are performed using the GMDH technique as found in commercially available software (e.g., "KnowledgeMiner 5.0" cited hereinabove and in Appendix A). The GMDH correlation equations for selected IS parameters (as shown in TABLE 4) and for FTIR oxidation data (i.e., total oxidation metric, the FTIR peak area calculations over the range of 1833–1640 cm$^{-1}$, as described above in reference to FIG. 18) are shown in the TABLE 5 below.

TABLE 5

Exemplary GMDH Equations Relating to Selected Statistical IS Parameters
and FTIR Oxidation Data

```
X2  - dZmaghigh
X33 - invzimag10Hz
X10 - TANDhigh
X31 - invzimag10kHz
X32 - invzimag100Hz
X13 - zreal10kHz
X28 - invzreal10Hz
X18 - zimag10kHz
X26 - invzreal10kHz
X12 - TANDvlow
X29 - invzreal100mHz
```

Figure 29:
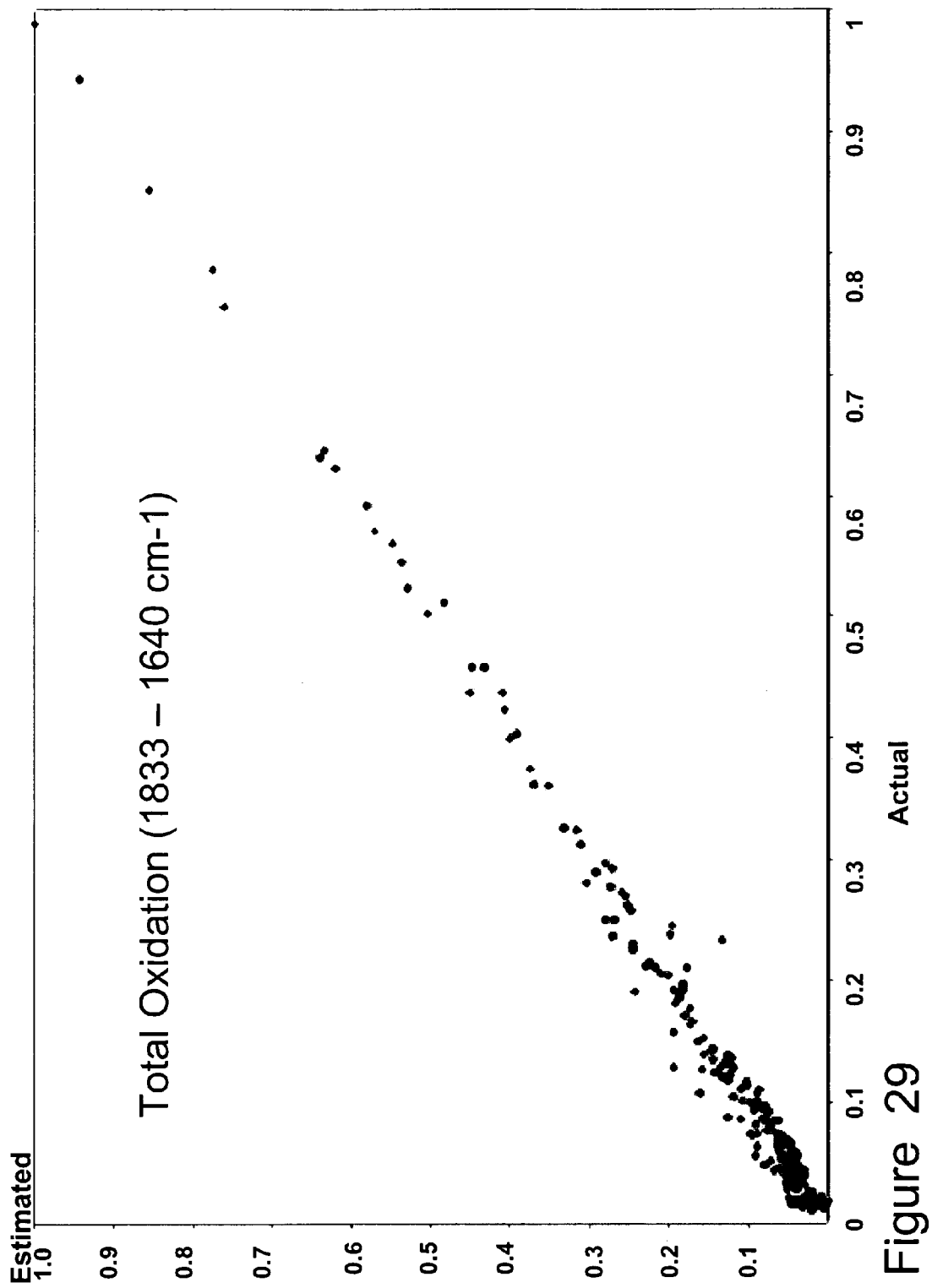
FIG. 29 is a plot of the correlation between FTIR oxidation data at 1833–1640 inverse-cm and impedance spectroscopy parameter data analyzed by GMDH with respect to oxidation.

$a12 = -2.567\mathrm{e}{+}7X26\hat{\;}2 - 7.406\mathrm{e}{+}10X28\hat{\;}2 + 4.173\mathrm{e}{+}10X26X28 + .402\mathrm{e}{+}4X26 - 2.763\mathrm{e}{+}0$
$a11 = -1.972\mathrm{e}{+}10X31\hat{\;}2 + 8.492\mathrm{e}{-}5X13 + 1.288\mathrm{e}{+}1X13X31 - 1.334\mathrm{e}{+}6X31 - 9.714\mathrm{e}{+}0$
$\quad z22 = +3.477\mathrm{e}{-}1a11\hat{\;}2 + 2.432\mathrm{e}{-}1a12\hat{\;}2 - 1.164\mathrm{e}{-}1a12 - 5.698\mathrm{e}{-}1a11a12 + 1.039\mathrm{e}{+}0a11$
$b12 = +1.219\mathrm{e}{-}9X18\hat{\;}2 + 6.031\mathrm{e}{+}7X32\hat{\;}2 + 4.736\mathrm{e}{+}4X32 + 2.370\mathrm{e}{-}1X18X32 + 3.374\mathrm{e}{-}4X18 + 2.268\mathrm{e}{+}1$
$b11 = -7.586\mathrm{e}{-}4X10\hat{\;}2 + 7.458\mathrm{e}{-}11X18\hat{\;}2 - 1.957\mathrm{e}{-}6X10X18 - 2.765\mathrm{e}{-}1X10 - 2.036\mathrm{e}{+}0$
$\quad z21 = -5.163\mathrm{e}{-}2b11\hat{\;}2 + 5.446\mathrm{e}{-}2b12\hat{\;}2 + 3.951\mathrm{e}{-}1b11 + 6.158\mathrm{e}{-}1b12$
$\quad z32 = +1.152\mathrm{e}{-}1z21z22 - 1.140\mathrm{e}{-}1z21\hat{\;}2 + 5.493\mathrm{e}{-}1z21 + 4.538\mathrm{e}{-}1z22$
$\quad z31 = -9.137\mathrm{e}{-}11X18\hat{\;}2 - 2.774\mathrm{e}{+}11X29\hat{\;}2 + 4.004\mathrm{e}{+}6X29 + 3.547\mathrm{e}{+}1X18X29 + 1.063\mathrm{e}{+}0$
$\quad z42 = -8.974\mathrm{e}{-}2z31\hat{\;}2 - 3.637\mathrm{e}{-}2z32\hat{\;}2 + 9.957\mathrm{e}{-}1z32 + 1.229\mathrm{e}{-}1z31z32$
$\quad z41 = +1.714\mathrm{e}{-}9X13\hat{\;}2 - 1.781\mathrm{e}{+}11X28\hat{\;}2 + 2.945\mathrm{e}{+}6X28 - 2.373\mathrm{e}{+}1X13X28 - 1.817\mathrm{e}{-}4X13 + 4.274\mathrm{e}{-}1$
$\quad\quad z52 = +3.067\mathrm{e}{-}2z41\hat{\;}2 - 2.644\mathrm{e}{-}2z42\hat{\;}2 - 1.507\mathrm{e}{-}1z41 + 1.130\mathrm{e}{+}0z42$
$\quad\quad z51 = +8.399\mathrm{e}{-}2X10 + 2.074\mathrm{e}{+}0$
$\quad\quad\quad z62 = +1.045\mathrm{e}{+}0z52 + 1.469\mathrm{e}{-}2z51z52 + 4.828\mathrm{e}{-}2z51$
$\quad\quad\quad z61 = +4.482\mathrm{e}{-}6X12\hat{\;}2 + 9.482\mathrm{e}{-}10X18\hat{\;}2 + 2.282\mathrm{e}{-}4X18 - 1.149\mathrm{e}{-}6X12X18 - 1.452\mathrm{e}{-}1X12 + 1.309\mathrm{e}{+}1$
$\quad\quad\quad\quad z72 = -1.300\mathrm{e}{-}1z61\hat{\;}2 - 1.177\mathrm{e}{-}1z62\hat{\;}2 + 9.555\mathrm{e}{-}1z62 + 2.547\mathrm{e}{-}1z61z62 + 4.900\mathrm{e}{-}2z61$
$c12 = -4.683\mathrm{e}{+}7X33\hat{\;}2 - 9.254\mathrm{e}{+}3X33 - 6.113\mathrm{e}{+}8X26X33 + 4.346\mathrm{e}{+}3X26 - 1.437\mathrm{e}{+}0$
$c11 = +4.025\mathrm{e}{-}10X13\hat{\;}2 + 5.941\mathrm{e}{-}10X18\hat{\;}2 + 2.238\mathrm{e}{-}4X18 - 1.723\mathrm{e}{-}9X13X18 - 2.438\mathrm{e}{-}4X13 + 1.845\mathrm{e}{+}1$
$\quad z71 = -1.462\mathrm{e}{-}1c11c12 + 1.322\mathrm{e}{-}1c11\hat{\;}2 + 1.007\mathrm{e}{+}0c11$
$\quad z82 = +6.888\mathrm{e}{-}1z71\hat{\;}2 + 6.488\mathrm{e}{-}1z72\hat{\;}2 + 1.366\mathrm{e}{+}0z72 - 1.341\mathrm{e}{+}0z71z72 - 3.724\mathrm{e}{-}1z71$
$\quad z81 = +1.714\mathrm{e}{-}9X13\hat{\;}2 - 1.781\mathrm{e}{+}11X28\hat{\;}2 + 2.945\mathrm{e}{+}6X28 - 2.373\mathrm{e}{+}1X13X28 - 1.817\mathrm{e}{-}4X13 + 4.274\mathrm{e}{-}1$
$\quad\quad z92 = -2.035\mathrm{e}{-}2z82\hat{\;}2 - 8.351\mathrm{e}{-}2z81 + 2.301\mathrm{e}{-}2z81z82 + 1.072\mathrm{e}{+}0z82$
$d12 = +1.439\mathrm{e}{+}7X32\hat{\;}2 + 1.842\mathrm{e}{+}4X32 - 7.550\mathrm{e}{+}5X31 - 6.500\mathrm{e}{+}0$
$d11 = +8.399\mathrm{e}{-}2X10 + 2.074\mathrm{e}{+}0$
$\quad z91 = -5.261\mathrm{e}{-}2d11\hat{\;}2 - 4.385\mathrm{e}{-}2d12\hat{\;}2 + 9.558\mathrm{e}{-}1d12 - 1.696\mathrm{e}{-}1d11d12$
$\quad\quad z102 = -9.407\mathrm{e}{-}2z92\hat{\;}2 - 3.684\mathrm{e}{-}1z91 + 9.376\mathrm{e}{-}2z91z92 + 1.366\mathrm{e}{+}0z92$
$\quad\quad z101 = -3.695\mathrm{e}{+}7X33\hat{\;}2 + 2.239\mathrm{e}{-}2X2X33 - 2.557\mathrm{e}{+}4X33 - 4.591\mathrm{e}{-}1$
Oxidation (FTIR) $= -9.297\mathrm{e}{-}2z101\hat{\;}2 + 8.430\mathrm{e}{-}2z102z102 + 5.460\mathrm{e}{-}1z101 + 6.145\mathrm{e}{+}0z102 + 5.019\mathrm{e}{+}0$ A plot of actual vs. predicted or estimated oxidation values determined from the selected IS parameters is shown in FIG. 29. The figure data includes data for both the ternary formulation and for the two new fluids with additional components. The oxidation values (also referred to equivalently herein as the oxidation metric, total oxidation metric or total carbonyl metric) are determined from the FTIR peak area calculations over the range of 1833–1640 cm$^{-1}$. In this example, the fluid property that can be determined from the exemplary IS parameters is the total oxidation, which may be related to formulation properties such as the selected additives and additive concentrations, as well as to the HOOT processing time.

EXAMPLE 6

Hot Oil Oxidation Test—Data Analysis Using Equivalent Circuit Modeling Combined with Statistical Techniques In yet another embodiment of the inventive concept, the IS data may be analyzed using a combination of equivalent circuit modeling and statistical techniques. In this aspect of the inventive concept, the frequency-dependent IS data are expressed in terms of frequency-independent circuit parameter values as exemplified in FIG. 30. This is accomplished using a Complex Non-Linear Least Squares (CNLLS) technique as described in the above section entitled "*Exemplary Data Analysis Using Equivalent Circuit Modeling*". Upon reduction, this model (FIG. 30) yields values for the electrically-active properties of the fluid, both static (bulk) and dynamic (interfacial reactivity). These IS parameters are derived for the ternary formulation (base oil plus ZDDP plus dispersant plus sulfonate detergent) and for the two new fluids with additional components (the ternary formulation plus: a) 1% phenate detergent; and, b) 1% phenate detergent and 1% viscosity index improver), and correlated against FTIR oxidation values using the GMDH technique as described above.

Figure 30:
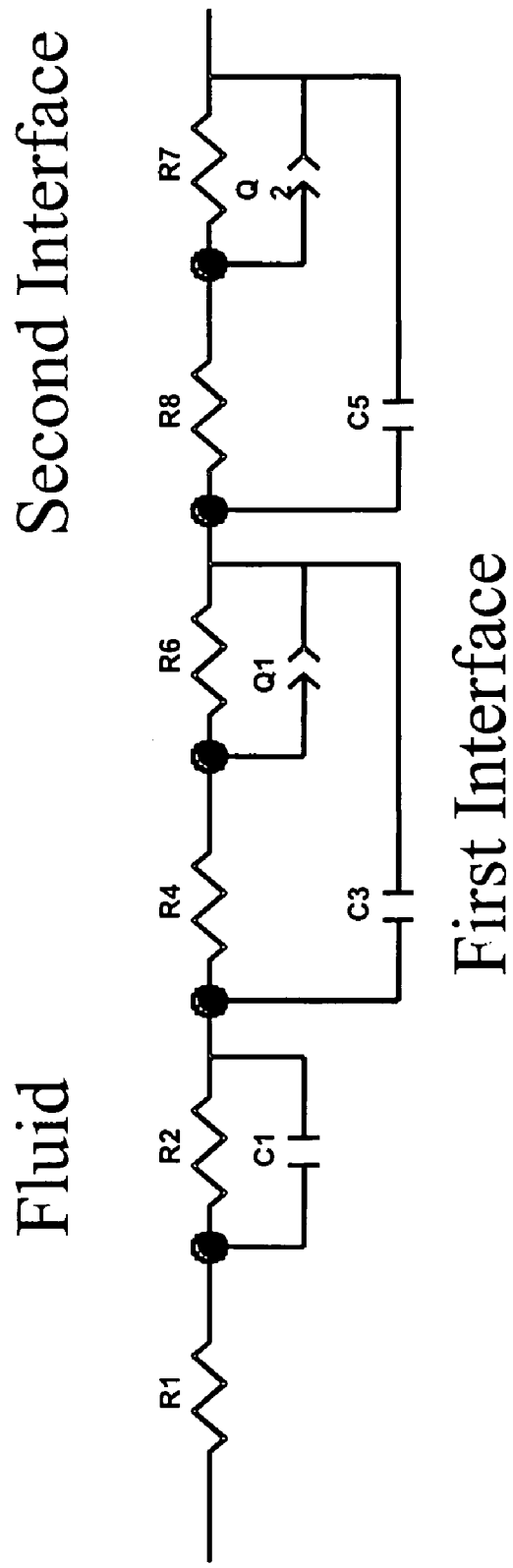
FIG. 30 is an illustration of a third alternative equivalent circuit for modeling impedance spectra data.

For this aspect of the inventive concept, TABLE 6 below shows the GMDH correlation equations using the equivalent circuit IS parameters of FIG. 30, and FTIR oxidation values. Persons skilled in the arts of data analysis will readily understand that any of the following equivalent circuit IS parameters could likewise be used in accordance with the example illustrated by TABLE 6: a bulk fluid resistance $R_{fluid}$, a bulk fluid capacitance $C_{fluid}$, a bulk fluid time constant $\tau_{fluid}$, an interface capacitance $C_{dl}$, a charge transfer resistance $R_{ct}$, an interface time constant $\tau_i$, an interface resistance $R_i$, a Constant Phase Element $Q_i$, a Constant Phase Element exponent n, a film time constant $\tau_{film}$, a film resistance $R_{film}$, and a film capacitance $C_{film}$.

TABLE 6

Figure 31:
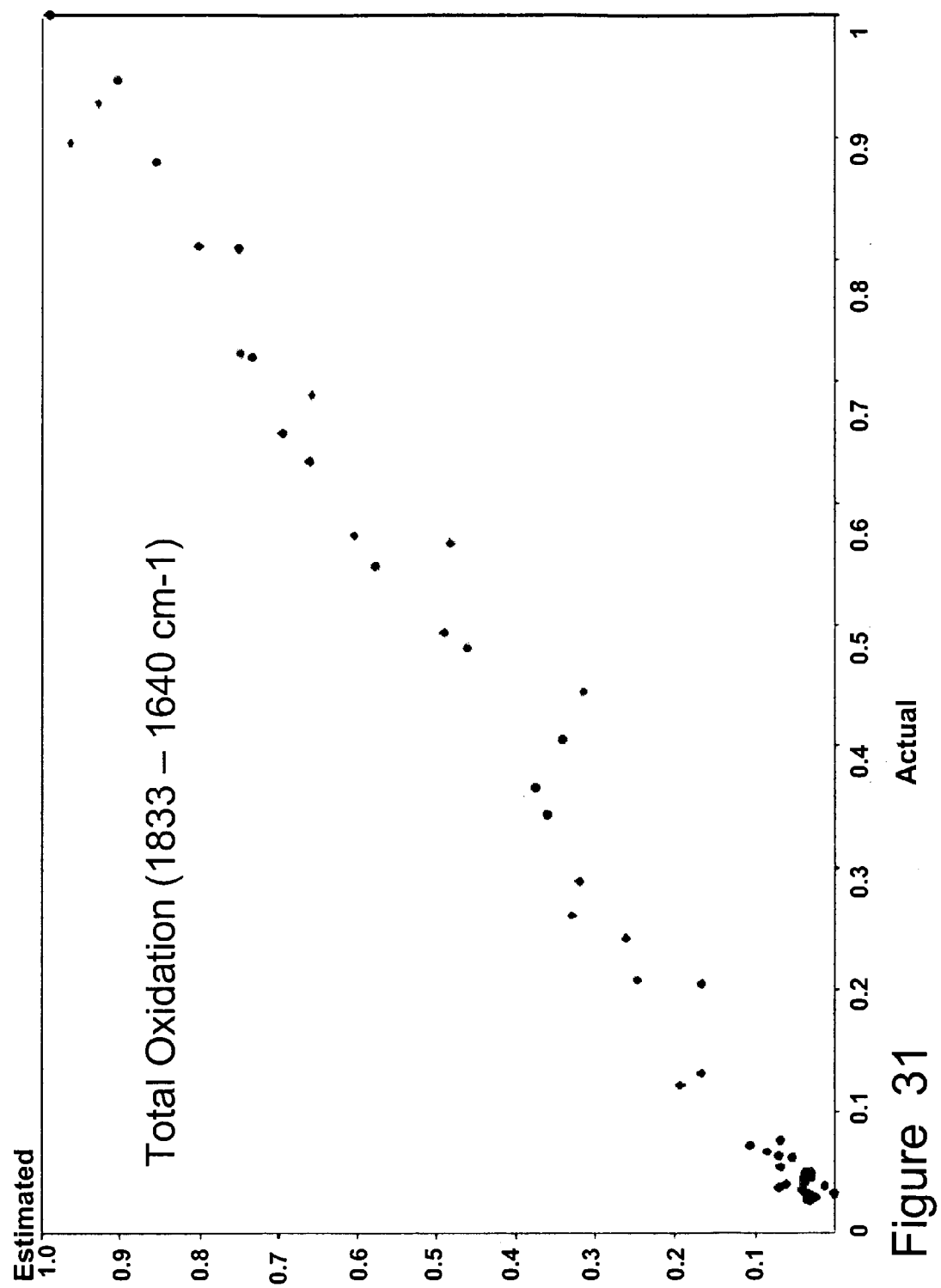
FIG. 31 is a plot of the correlation between FTIR oxidation data at 1833–1640 inverse-cm and impedance spectroscopy equivalent circuit parameter data analyzed by GMDH with respect to oxidation.

Exemplary GMDH Equations Relating Selected Equivalent Circuit IS Parameters and FTIR Oxidation Data $X7 = Q1$
$X9 = R8$
$X11 = R7$
$X3 = C1$
$X12 = Q2$
$X4 = R4$
$X6 = R6$
$X2 = R2$
$X10 = C5$
$z11 = + 2.10922 \times 10^{13} \times X3 X12 - 1.10256 \times 10^{18} \times X3 X3 - 2.43898 \times 10^{6} \times X12^2 - 7.53010 \times 10^{-1}$
$z12 = + 4.24133 \times 10^{3} \times X12 + 1.92502 \times 10^{-2} \times X4 X12 - 3.27766 \times 10^{6} X12^2 - 6.99263 \times 10^{-1}$
$z21a = + 2.77658 \times 10^{3} \times X12 - 8.22530 \times 10^{-1}$
$z21b = + 3.81709 \times 10^{5} \times X7 - 1.27437$
$z22a = + 1.6392 \times z11 - 6.30134 \times 10^{-1} \times z12 + 7.50432 \times 10^{-1} \times z11 \times z12 - 5.77612 \times 10^{-1} \times z11^2$
$za32 = + 9.32239 \times 10^{-1} \times z22 - 3.62732 \times 10^{-1} \times z21a \times z22 + 2.13920 \times 10^{-1} \times z22^2$
$zc31 = - 2.68192 \times 10^{7} \times X6 + 6.79587 \times 10^{5} \times X7 - 6.55073 \times 10^{10} \times X7^2 - 9.40777 \times 10^{-1}$
$zb32 = + 9.10268 \times 10^{-1} \times z22a - 1.74415 \times 10^{-1} \times z21b^2 + 1.36023 \times 10^{-1} \times z22a^2$
$za42 = - 1.25133 \times 10^{-1} \times z21a + 1.08294 \times za32$
$zb42 = + 3.18639 \times 10^{-1} \times zc31 + 8.45805 \times 10^{-1} \times zb32 + 3.05694 \times 10^{-1} \times zc31 \times zb32 - 8.15632 \times 10^{-2} \times zb32^2$
$za51 = + 4.55819 \times 10^{-12} \times X11 + 5.16039 \times 10^{3} \times X12 - 2.84055 \times 10^{-24} \times X11^2 - 3.80058 \times 10^{6} \times X12^2 - 7.74618 \times 10^{-1}$
$za52 = + 3.51598 \times 10^{-1} \times za41 + 8.59137 \times 10^{-1} \times za42 + 3.57450 \times 10^{-1} \times za41 \times za42 - 1.25593 \times 10^{-1} \times za42^2$
$zb51 = + 1.02189 \times zb22 - 9.31893 \times 10^{-2} \times zb21 \times zb22$
$zb52 = + 3.70104 \times 10^{-1} \times za42 + 6.40380 \times 10^{-1} \times zb42$
$za61 = - 3.52579 \times 10^{-1} \times za51 + 1.29288 \times za52 - 1.37206 \times 10^{-1} \times za51^2$
$zb62 = - 1.14779 \times zb51 + 2.16861 \times zb52 + 9.21526 \times zb51 \times zb52 - 4.75962 \times zb51^2 - 4.48006 \times zb52^2$
$z72 = + 4.95926 \times 10^{}1 \times za61 + 5.13511 \times 10^{}1 \times zb62$
$z71 = + 5.74734 \times 10^{}1 \times zb32 + 4.32448 \times 10^{}1 \times za32$
$z81 = + 3.79240 \times 10^{}12 X11 - 2.22245 \times 10^{}1$
$z82 = - 7.54167 \times 10^{**}1 \times z71 + 1.72484 \times \times z72$
$z91 = + 5.51207 \times 10^{}6 X9 - 7.51330 \times 10^{}1$
$z92 = + 9.93505 \times 10^{}1 \times z82 + 1.47721 \times 10^{}2 \times z81 \times z81$
$z101 = + 3.81709 \times 10^{5} \times X7 - 1.27437$
$z102 = - 5.61370 \times 10^{2} \times z91 + 9.88742 \times 10^{-1} \times z92 - 5.29448 \times 10^{-2} \times z91 \times z92$
$\text{Oxidation(FTIR)} = + 3.42695 \times 10^{3} \times z102 + 1.27275 \times 10^{2} \times z101^2 - 1.08217 \times 10^{2} \times z102^2 + 3.12363 \times 10^{*3}$ A plot of actual vs. predicted, or estimated, oxidation values determined from the selected equivalent circuit IS parameters is shown in FIG. 31. The figure data includes data for both the ternary formulation and for the two new fluids with additional components. The actual oxidation values are determined from the FTIR peak area calculations over the range of 1833–1640 $cm^{-1}$ as previously described. In this example, the fluid property that can be determined from the exemplary IS parameters is the total oxidation metric, which may be related to formulation properties such as the selected additives and additive concentrations, as well as to the HOOT processing time.

Formulation Design Improvement

The examples set forth above demonstrate how the practice of the present invention provides extensive information about fluid properties. Persons skilled in the arts of lubricating fluids shall appreciate that these methods may be implemented in many ways for the purpose of improving the design of fluid formulations and developing new formulations.

In one embodiment of the inventive concept, the methods described above can be used to design fluid formulations having improved lifetimes under oxidative stress. This may be accomplished using HOOT processing on a plurality of fluid formulations having differing additives, additive combinations, and additive concentrations. Using the IS measurements and data analysis methods, the formulations having the highest resistance to oxidative stress may be determined and related to the formulation properties. This information can then be used to design improved formulations.

In yet another embodiment of the present inventive concept, the methods set forth above can be used to improve the design of lubricant detergents. Lubricant detergents comprise additives that contain a soap portion incorporated with a metal carbonate in an oil matrix. It is observed from IS measurements and data analyses that there is a relationship between the interfacial impedance and the amount of carbonate present. This is observed in experiments where the detergent concentration is varied in a new oil (e.g., see TABLE 2) as well as when the carbonate is reacted out in an oxidation experiment (e.g., see FIG. 27). As the amount of carbonate is depleted, a corresponding decrease in the interfacial impedance is observed. These data may be interpreted to indicate that the anti-wear properties of the overbased sulfonate-detergent are related to the interfacial behavior of the carbonate incorporated in the additive, and not necessarily the soap portion.

In an embodiment of the inventive concept, formulations may be designed wherein the properties influenced by the sulfonate-detergent additives are selectively modified. For example, the additives may be selectively modified to improve the anti-wear behavior, or to adjust interface reactivity effects. Adjustments to the carbonate incorporation methods may be used to make such modifications and improvements. These adjustments may include changing the soap-to-carbonate ratio, the detergent overbase ratio, the carbonate-metal counter ion, or the hydrocarbon size of the soap. For each additive adjustment, the inventive methods taught herein may be used to determine the desired effect of the adjustment, for example, by determining the corresponding change in the interface reactivity fluid property. An improved additive and formulation may thereby be developed in accordance with the inventive process. Many other implementations of the present inventive teachings used to improve the design of lubricant formulations will be readily apparent to persons skilled in the arts of lubricating fluid development and production.

Exemplary Formulations

Although the practice of the present inventive concept is not limited to lubricating fluids, many advantageous embodiments may include lubricating fluid formulations. A lubricating fluid formulation may consist of a base oil (BO) incorporating one or more lubricant additives. Exemplary BO types may include, without limitation, the following categories: mineral base and synthetic base. Exemplary lubricant additive types may include, without limitation, the following lubricant additive categories: viscosity modifiers, pour point depressants, stabilizers, seal swell agents, anti-static additives, antioxidants, metal deactivators, anti-foam agents, detergents, dispersants, anti-wear additives, and corrosion inhibitors.

Other exemplary fluids that may be used with embodiments of the present inventive concept may include, without limitation, lubricant additive packages, fuel treatment additives and top treatments. These exemplary fluids may include a dilutant (such as kerosene or other fuel), and at least one additive, wherein a typical additive may include, without limitation, the following categories: viscosity modifiers, pour point depressants, stabilizers, seal swell agents, anti-static additives, antioxidants, metal deactivators, anti-foam agents, detergents, dispersants, anti-wear additives, and corrosion inhibitors. A top treatment may include an additive (such a DI, VII, etc.) and a dilutant or BO.

Exemplary Fluid Properties

Many examples of fluid properties have been presented hereinabove. In reference to the present inventive concept, fluid properties may include any physicochemical metric indicative of the physical or chemical properties of the fluids. Examples of such physicochemical metrics include, without limitation, the following: an interface reaction rate; a bulk resistivity; an ion concentration; an ion mobility; a surface film formation; a total oxidation level; a P—O—C bond concentration; a P═S bond concentration; a ZDDP concentration; and a carbonate concentration. Persons skilled in the arts of physics, chemistry and physical chemistry will understand that these are just a few of the possible fluid properties encompassed by the present teachings.

Exemplary Method of Operation

Figure 32:
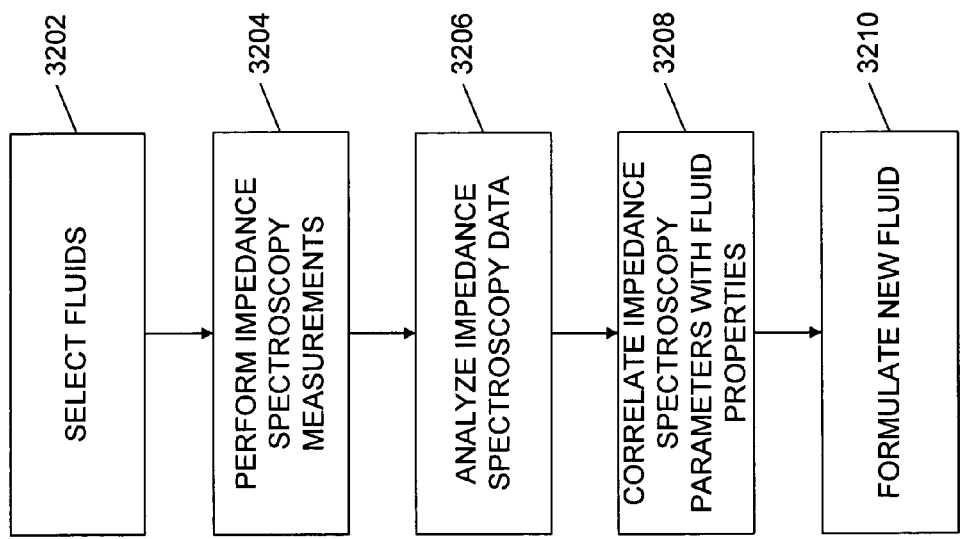
FIG. 32 is a flowchart diagram illustrating an exemplary method for evaluating and improving the properties of fluids in accordance with the present inventive concept.

In accordance with the present invention, an exemplary method for evaluating and improving a fluid formulation is described. The STEPS 3202 to 3210 described below are illustrated in the flowchart diagram of FIG. 32.

At a STEP 3202, a set of fluids representative of a fluid formulation may be selected. In one exemplary embodiment, each fluid in the set may comprise a base fluid incorporating one or more additives at one or more concentration levels. In another exemplary embodiment, each fluid may comprise a sample from a HOOT process series. The method proceeds to a STEP 3204.

At the STEP 3204, IS measurements are performed on each of the fluids to provide IS data. The IS data may include at least three points, and typically include tens or hundreds of points. More than a few hundred points are not usually required. In general, the IS data include frequencies both above and below 1Hz, over a range of frequencies sufficient to define IS parameters associated with both the bulk and interface of the fluids. The method proceeds to a STEP 3206.

At the STEP 3206, the IS data are analyzed using statistical techniques, equivalent circuit modeling techniques, or a combination thereof. The data analysis provides IS parameters indicative of at least one fluid property for the fluids. The method proceeds to a STEP 3208.

At the STEP 3208, a correlation is determined between selected IS parameters and selected properties of the fluids. As one example, a correlation may be determined between the IS parameter dZmaglow and the carbonate concentrations in the fluids. As another example, a plurality of IS parameters may be correlated to total oxidation levels or values for the fluids. As shown by the teachings herein, a plurality IS parameters may be obtained, and these parameters may be correlated singly or in combination to a plurality of fluid properties. The method then proceeds to a STEP 3210.

At the STEP 3210, a new fluid formulation is developed, responsive to the correlation between the selected IS parameters and the selected properties of the fluids. Examples for producing a new, or modified, fluid formulation include, without limitation, the following: adding at least one additive; removing at least one additive; modifying the concentration of at least one additive; modifying a soap-to-carbonate ratio of a detergent additive; modifying a detergent overbase ratio of a detergent additive; modifying a carbonate-metal counter ion of a detergent additive; and modifying a hydrocarbon size of a detergent additive. Many other examples in accordance with the present teachings will be apparent to persons skilled in the arts of developing industrial fluid formulations.

The above description is intended to be illustrative and not restrictive. Many embodiments and applications other than the examples provided would be apparent to those of skill in the art upon reading the above description. The scope of the invention should be determined, not with reference to the above description, but should instead be determined with reference to the appended claims, along with the full scope of equivalents to which such claims are entitled. It is anticipated and intended that future developments will occur in the field of determining fluid properties and IS parameters using impedance spectroscopy and that the disclosed systems and methods will be incorporated into such future embodiments. Accordingly, it will be understood that the invention is capable of modification and variation and is limited only by the following claims.

What is claimed is:

1. A fluid formulation evaluation and improvement method, comprising the steps of:
   a) obtaining a plurality of fluids representative of a first fluid formulation;
   b) obtaining impedance spectroscopy (IS) data for each of the fluids, wherein the IS data include data at not less than three frequencies;
   c) analyzing the IS data using statistical techniques to produce at least one IS parameter indicative of at least one fluid property for each of the fluids;
   d) determining at least one correlation between the at least one IS parameter and the at least one fluid property; and
   e) producing a second fluid formulation responsive to the at least one correlation.

2. The fluid formulation evaluation and improvement method of claim 1, wherein the plurality of fluids include fluids having selected concentrations of at least one additive in a base fluid.

3. The fluid formulation evaluation and improvement method of claim 2, wherein the base fluid is a lubricant base oil.

4. The fluid formulation evaluation and improvement method of claim 2, wherein the at least one additive is a lubricant additive.

5. The fluid formulation evaluation and improvement method of claim 4, wherein the plurality of fluids include fluids obtained from a thermal decomposition test.

6. The fluid formulation evaluation and improvement method of claim 4, wherein the plurality of fluids include fluids obtained from a Hot Oil Oxidation Test.

7. The fluid formulation evaluation and improvement method of claim 1 wherein the at least three frequencies include at least one frequency less than one Hertz, and at least one frequency greater than one Hertz.

8. The fluid formulation evaluation and improvement method of claim 1, wherein the step of analyzing the IS data includes performing equivalent circuit modeling.

9. The fluid formulation evaluation and improvement method of claim 1, wherein the statistical techniques include at least one of the following techniques: Principal Component Analysis; Multivariate Least Squares Regression; Principal Component Regression; Pattern Recognition analysis; Cluster analysis; Neural Net analysis; and Group Methods of Data Handling.

10. The fluid formulation evaluation and improvement method of claim 1, wherein the at least one IS parameter includes at least one equivalent circuit IS parameter.

11. The fluid formulation evaluation and improvement method of claim 1, wherein the at least one IS parameter includes at least one statistical IS parameter.

12. The fluid formulation evaluation and improvement method of claim 1, wherein the at least one fluid property is a physicochemical metric indicative of one of (a) the chemical and (b) the physical properties of the plurality of fluids.

13. The fluid formulation evaluation and improvement method of claim 1, wherein the first fluid formulation is selected from the following categories: lubricants, lubricant additive packages; fuel treatment additives; and top treatments.

14. The fluid formulation evaluation and improvement method of claim 13, wherein the plurality of fluids include fluids having selected concentrations of at least one additive in a base fluid.

15. The fluid formulation evaluation and improvement method of claim 14, wherein the base fluid is a dilutant.

16. The fluid formulation evaluation and improvement method of claim 14, wherein the base fluid is a base oil.

17. The fluid formulation evaluation and improvement method of claim 14, wherein the at least one additive is a lubricant additive.

18. A fluid formulation evaluation and improvement system, comprising:
   a) an impedance spectroscopy (IS) probe operatively disposed in contact with a fluid selected from a plurality of fluids representative of a first fluid formulation;
   b) an impedance spectrometer, operatively coupled to the IS probe, wherein the impedance spectrometer sequentially performs impedance measurements on each of the plurality of fluids, and wherein the impedance spectrometer produces IS data at not less than three distinct frequencies for each of the plurality of fluids;
   c) a data processing system, operatively coupled to receive the IS data from the impedance spectrometer, wherein the data processing system determines IS parameter data including at least one IS parameter for each of the plurality of fluids using statistical techniques; and
   d) a Formulation Design Operator, operatively disposed to receive the IS parameter data, and wherein the Formulation Design Operator determines at least one correlation between the IS parameter data and at least one fluid property, for each of the plurality of fluids, and wherein the Formulation Design Operator produces a second fluid formulation responsive to the at least one correlation.

19. The fluid formulation evaluation and improvement system of claim 18, wherein the IS prode includes concentric tubular electrodes.

20. The fluid formulation evaluation and improvement system of claim 18, wherein the IS prode includes interdigitated electrodes.

21. The fluid formulation evaluation and improvement system of claim 18, wherein the IS prode includes spiral electrodes.

22. The fluid formulation evaluation and improvement system of claim 18 wherein the IS prode includes parallel plate electrodes.

23. The fluid formulation evaluation and improvement system of claim 18, wherein the data processing system is configured to determine an equivalent circuit model from at least some of the IS data.

24. The fluid formulation evaluation and improvement system of claim 18, further comprising a temperature controller, operatively coupled to control the temperature of the fluid selected from a plurality of fluids.

25. The fluid formulation evaluation and improvement system of claim 18, wherein the Formulation Design Operator includes at least one person.

26. The fluid formulation evaluation and improvement system of claim 18, wherein the second fluid formulation is a lubricant oil having at least one lubricant additive.

27. The fluid formulation evaluation and improvement method of claim 18, wherein the first fluid formulation is selected from the following categories: lubricant additive packages; fuel treatment additives; and top treatments.

28. A fluid formulation evaluation and improvement system, comprising:
   a) means for obtaining a plurality of fluids representative of a first fluid formulation;
   b) means for obtaining impedance spectroscopy (IS) data for each of the fluids, wherein the IS data include data at at least three frequencies;
   c) means for analyzing the IS data using statistical tecniques to produce at least one IS parameter indicative of at least one fluid property for each of the fluids;
   d) means for determining at least one correlation between the at least one IS parameter and the at least one fluid property; and
   e) means for producing a second fluid formulation responsive to the at least one correlation.

29. The system of claim 28, wherein means (c) further functions to determine an equivalent circuit model from at least some of the IS data.

* * * * *

UNITED STATES PATENT AND TRADEMARK OFFICE
CERTIFICATE OF CORRECTION

| | | |
|---|---|---|
| PATENT NO. | : 7,078,910 B2 | Page 1 of 1 |
| APPLICATION NO. | : 10/793344 | |
| DATED | : July 18, 2006 | |
| INVENTOR(S) | : Hirthe et al. | |

It is certified that error appears in the above-identified patent and that said Letters Patent is hereby corrected as shown below:

Col. 26
Claim 28, line 49 "at least", should read --not less than--.

Signed and Sealed this

Tenth Day of April, 2007

JON W. DUDAS
*Director of the United States Patent and Trademark Office*